United States Patent [19]
Goble

[11] Patent Number: 5,431,651
[45] Date of Patent: Jul. 11, 1995

[54] CROSS PIN AND SET SCREW FEMORAL AND TIBIAL FIXATION METHOD

[76] Inventor: E. Marlowe Goble, 850 E. 1200 North, Logan, Utah 84321

[21] Appl. No.: 14,532

[22] Filed: Feb. 8, 1993

[51] Int. Cl.⁶ ............................................. A61F 5/04
[52] U.S. Cl. ...................................... 606/73; 606/72; 606/96; 606/99; 606/102
[58] Field of Search ................... 606/98, 96, 97, 64, 606/65, 73, 99, 102, 104, 105, 80, 72; 623/13, 20

[56] References Cited

U.S. PATENT DOCUMENTS

| | | |
|---|---|---|
| 4,257,411 | 3/1981 | Cho . |
| 4,535,768 | 8/1985 | Hourahane et al. . |
| 4,668,233 | 5/1987 | Seedhom et al. . |
| 4,672,957 | 6/1987 | Hourahane . |
| 4,739,751 | 4/1988 | Sapega et al. . |
| 4,823,780 | 4/1989 | Odensten et al. . |
| 4,901,711 | 2/1990 | Goble et al. . |
| 4,920,958 | 5/1990 | Walt et al. . |
| 4,927,421 | 5/1990 | Goble et al. ........................ 606/73 |
| 4,950,270 | 8/1990 | Bowman et al. ..................... 606/72 |
| 4,985,032 | 1/1991 | Goble . |
| 5,037,426 | 8/1991 | Goble et al. ........................ 606/96 |
| 5,139,520 | 8/1992 | Rosenberg ........................... 623/13 |
| 5,152,764 | 10/1992 | Goble . |
| 5,152,790 | 10/1992 | Rosenberg et al. ................. 623/13 |
| 5,211,647 | 5/1993 | Schmieding ....................... 606/104 |
| 5,234,434 | 8/1993 | Goble et al. ........................ 606/96 |
| 5,300,077 | 4/1994 | Howell .............................. 606/96 |

FOREIGN PATENT DOCUMENTS
0126520 2/1984 European Pat. Off. .
2078528 6/1981 United Kingdom .

*Primary Examiner*—Peter A. Aschenbrenner
*Assistant Examiner*—Guy V. Tucker
*Attorney, Agent, or Firm*—M. Reid Russell

[57] ABSTRACT

The invention is in a cross pin and set screw femoral and tibial fixation apparatus and method for mounting a ligament graft that, in one embodiment is a bone tendon bone type ligament graft and in another embodiment is a soft tissue ligament graft, in femoral and tibial tunnel sections of a straight ligament tunnel formed in an arthroscopic cruciate ligament replacement procedure. The apparatus and the steps involved in its use include, a drill guide for drilling a transverse hole or holes, which drill guide is arranged to be releasable from a first twist drill so as to leave it in place, the first twist drill to be used for guiding further drilling and passage of a fastener device. A K-wire, or the first twist drill if left in place, is then used for guiding a second twist drill, for enlarging the transverse hole and is used for guiding turning of a cannulated fastener device, that is a set screw or screw, into the femoral bone end of the ligament graft that has been fitted into the femoral tunnel section, providing a cross pin mounting to the femoral bone end of the bone tendon bone type ligament graft, or, utilizing the transverse hole, the apparatus of the invention can be used to provide a cross pin type mounting of a soft tissue ligament graft that is looped over the cross pin.

32 Claims, 16 Drawing Sheets

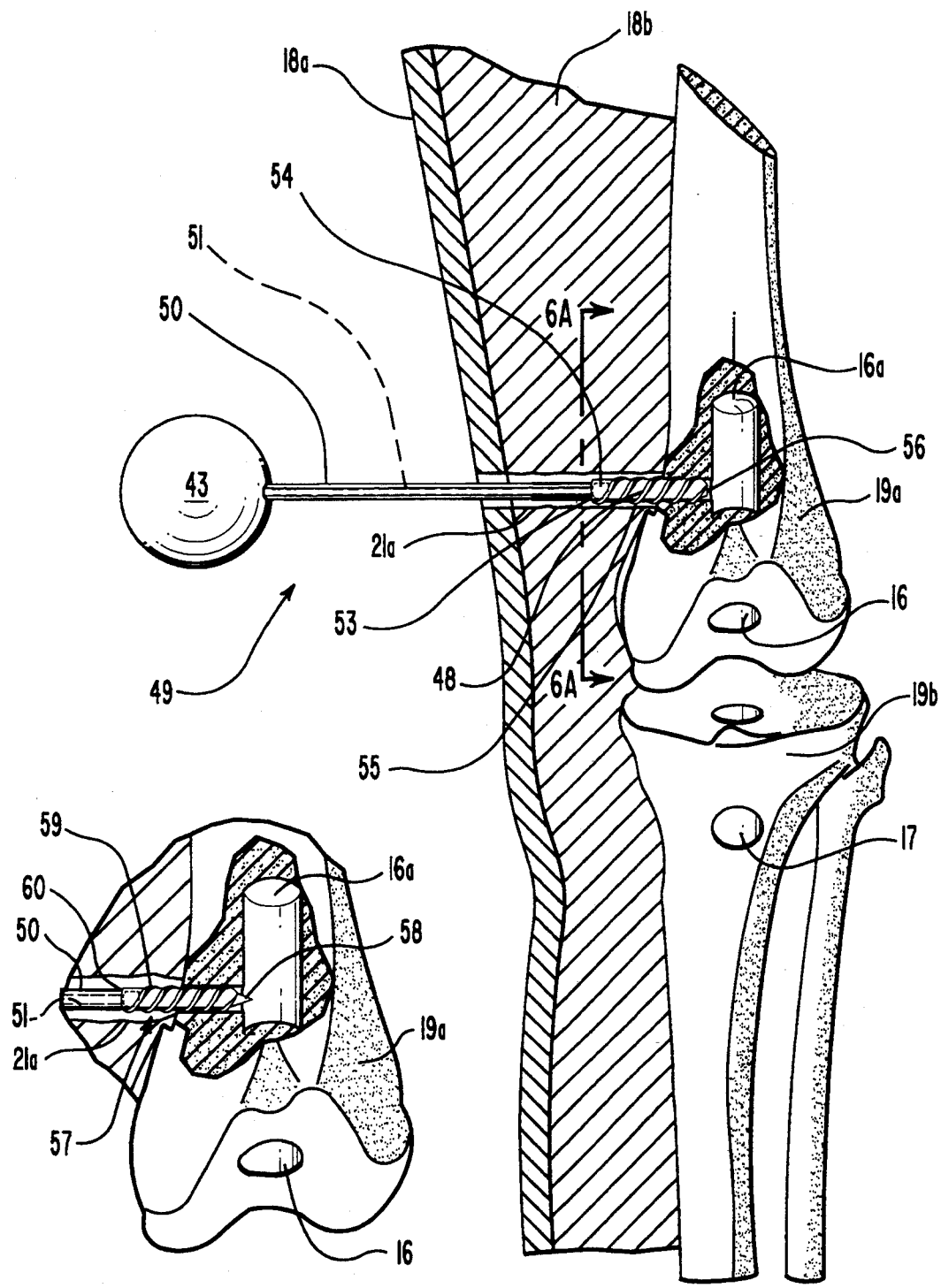
FIG. 6B
FIG. 6
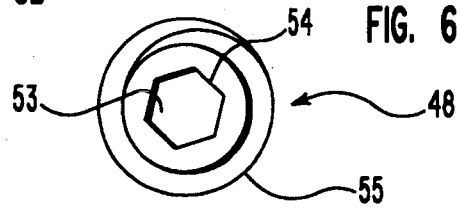
FIG. 6A

CROSS PIN AND SET SCREW FEMORAL AND TIBIAL FIXATION METHOD

BACKGROUND OF THE INVENTION

1. Field of the Invention

This invention relates to surgical procedures and apparatus utilized in arthroscopic surgical procedures for knee reconstructive surgery utilizing a drill guiding device for drilling a hole from the medial or lateral side of the knee to intersect a straight ligament tunnel for passing a fastener device to engage and endosteally mount a bone end of a bone tendon bone or other type of ligament graft in position in the ligament tunnel.

2. Prior Art

The invention is for use in an anterior or posterior cruciate ligament repair and replacement surgical procedure where tibial and femoral tunnel sections are formed to pass through the ligament points of origin in the knee, the tunnel sections for containing a ligament spanning the knee intra articular joint. With the knee bent to approximately ninety (90) degrees, the tibial and femoral tunnel sections form approximately a straight tunnel, facilitating fitting a ligament end into the femoral tunnel section. To provide a set screw, interference, or transverse pin type mounting of an end of a ligament graft in a either the femoral or tibial tunnel sections, a drill guide is utilized to form a transverse passage or hole that intersects a femoral and/or tibial tunnel section. Drill guides appropriate for use in providing this transverse drilling are shown in earlier U.S. patents of the inventor, U.S. Pat. Nos 4,901,711, 4,985,032 and 5,152,764, and in a U.S. Patent Application for a Multiple Guide Sleeve Drill Guide, U.S. Ser. No. 07/930,273. These drill guides each provide for drilling, from a guide sleeve device fitted to an external drill guide rod or leg, a straight hole or tunnel to intersect a target point on a drill guide reference rod or leg that is seated within the tunnel. An additional drill guide of the present inventor, identified as a "Sight Barrel Arthroscopic Instrument", U.S. patent application Ser. No. 07/580,172, is preferred for use in the invention for forming a transverse hole from within the knee to intersect, at an acute angle, a single point along a tunnel section, or points along both femoral and tibial tunnel sections.

The above cited drill guides of the inventor all reference the aligned tibial and femoral tunnel sections utilizing a reference rod that is fitted into the straight ligament tunnel. A practice of the method of the present invention utilizes a drill guide to drill from an external rod to a target on the reference rod, which drilling is accomplished utilizing a drill that includes indices scribed therealong for determining the exact distance from the side of the patent's knee to the ligament tunnel wall. Which measure is use to select an appropriate length of fastener device for seating in a ligament position in the ligament tunnel. Further unique to the invention, after drilling a transverse hole or passage to the ligament tunnel, the drill guide is replaced with a soft tissue guide for maintaining hole or passage location and to allow for twist drill replacement with a K-wire. The K-wire or, alternatively, the twist drill that was used with the drill guide to drill the transverse hole, doubling as a guide, is then used for guiding turning of a second twist drill therealong. The second twist drill provides for enlargement of the transverse hole and for guiding a cannulated screw or set screw fitted into the transverse hole that, depending upon placement, functions as a set, cross or interference screw, for securing a bone end of a bone tendon bone ligament graft, or other ligament graft, in the femoral ligament tunnel. The cannulated set screw can guide passage of a cross pin to pass through the ligament, providing additional purchase for mounting a bone tendon bone ligament graft, or can be utilized for fitting through a loop of a soft tissue graft that has been fitted into the femoral tunnel section. The cannulated set screw can also serve as a mount for a cleated washer that, when the set screw is turned into the tunnel section, guides the washer cleats into the side of a soft tissue graft fitted therein, urging it against the opposite tunnel wall.

The present process preferably utilizes a drill guide, like those set out above, for forming a transverse passage or hole that intersects a ligament mounting tunnel. While other drill guides have been utilized in arthroscopic surgical procedures, such have provided for drilling, from without the knee, to a locator point within the knee intra articular joint, rather than to a point within a ligament tunnel. Examples of such earlier devices are shown in patents to Walt, et al, U.S. Pat. No. 4,920,958; to Sapega, et al, U.S. Pat. No. 4,739,751; to Cho, U.S. Pat. No. 4,257,411; to Hourahane, et al, U.S. Pat. No. 4,535,768; to Hourahane, et al, U.S. Pat. No. 4,672,957; and a United Kingdom patent to Lovell, et al, No. 2,078,528. Also, other devices for drilling tibial and femoral tunnel sections are shown in patents to Odensten, et al, U.S. Pat. No. 4,823,780; Seedholm, et al, U.S. Pat. No. 4,668,233; and a European patent application No. 0126520. None of which patents, however, provide an arrangement that is suitable for practicing the method of the invention.

SUMMARY OF THE INVENTION

It is a principal object of the present invention in a cross pin and set screw femoral and tibial fixation method and apparatus for use in a knee arthroscopic surgical procedure, for forming a transverse hole from the medial or lateral side of the knee to intersect a prepared femoral or tibial tunnel section of a straight ligament tunnel and for fitting and guiding a fastener device, such as a set screw, interference screw or cross pin therethrough to engage and mount an end of a ligament graft in that tunnel section.

Another object of the present invention is to provide apparatus for forming a traverse hole to intersection a femoral or tibial tunnel section of a straight ligament tunnel, and for maintaining the integrity of that transverse and providing a guide for enlarging the transverse hole, as required, and for guiding passage of a cannulated fastener to the tunnel section to provide for securing an end of a ligament graft therein.

Another object of the present invention is to provide with a use of the apparatus and practice of the method of the invention for mounting a bone end of a bone tendon bone type ligament graft in a femoral section of the straight ligament tunnel utilizing a cannulated set or interference screw or cross pin.

Another object of the present invention is to provide, for obtaining additional purchase of a bone end of the bone tendon bone type ligament graft in the femoral tunnel section that includes a cannulated set screw mounting where the center longitudinal hole through the set screw is used as a guide for passing a pin therethrough that is urged through the bone end and into the opposite tunnel section wall, as a cross pin mounting, providing additional purchase.

Another object of the present invention is to provide, for use in a practice of the present method, a pushing device for moving a bone end of a bone tendon bone type ligament graft from a tibial tunnel section entry, across the intra articular joint, to the end of the femoral tunnel section, whereat the pushing device is removed, the bone end to receive a fastener device, that has been fitted through the transverse hole, to secure it in the femoral tunnel section.

Another object of the present invention is to provide a twist drill that is used as the first drill that includes indices scribed at equal spaced therealong indicated increments of length that are used for reading the depth of drill penetration to the ligament tunnel section, which determined depth is for use in selection of a length of fastener device.

Still another object of the invention is to provide for a utilization of the first twist drill as a guide for passing a cannulated twist drill therealong the provide for enlargement of the transverse hole, and to guide passage of the cannulated fastener device therealong.

Still another object of the invention is to provide for a utilization of a cannulated set screw turned into the transverse hole to the tunnel section as a guide for passing a K-wire, or the like, therethrough to travel, as a cross pin, through a ligament graft end or through a loop in a ligament graft into the opposite tunnel wall, providing ligament mounting or additional mounting purchase.

Still another object of the present invention is to provide, in a practice of the process of the invention, for maintaining the transverse hole in an open state by replacing of the first twist drill with a K-wire that is used for guiding over-drilling of the transverse hole and for guiding the fastener device along the transverse hole to the tunnel section in anticipation of fitting the bone end of a bone tendon bone ligament graft therein, whereafter the fastener device is urged into the bone end.

Still another object of the present invention is to provide, as a mounting for a soft. tissue graft, for fitting a cleated washer onto the end of a cannulated set screw that has been turned into the a transverse hole to the femoral tunnel section, whereby further turning of the set screw into the femoral tunnel section urges the washer cleats into the side of the soft tissue graft, mounting it therein.

Still another object of the present invention is to provide apparatus and a process for forming, from either the medial or lateral side of a patient's knee, a transverse hole to intersect a femoral or tibial tunnel section for passing a fastener device to engage a bone end of a bone tendon bone type ligament graft installed in the tunnel section, as a permanent ligament end mounting.

Still another object of the present invention is to provide apparatus and a method for its use for providing a fixation under tension of bone ends of a bone tendon bone type ligament graft in femoral and tibial tunnel sections of a straight ligament tunnel.

The cross pin and set screw femoral and tibial fixation apparatus and method of the invention are for use in an arthroscopic surgical procedure for replacement of a knee anterior or posterior cruciate ligament with a ligament graft. The graft is for installation in a straight ligament tunnel that is open at a tibial section end, passes through the knee intra articular joint, and into a femur section that ends in the femur endosteum. To provide for graft fixation in the respective tibial and femoral tunnel sections, a drill guide is used to drilling a transverse hole or holes to intersect the femoral tunnel section, and, depending upon the mounting strategy to be employed, to the tibial tunnel section. A preferred drill guide for use in the invention is that patented by the inventor, identified as a Multiple Guide Sleeve Drill Guide, U.S. patent application Ser. No. 07/930,273, that includes a straight reference rod or leg, that is for sliding into the straight ligament tunnel, and an external rod or leg that includes guide sleeves for positioning at spaced points along the external rod for guiding drilling of transverse holes utilizing twist drills. The drilling to pass through either the medial or lateral sides of the knee to intersect an aiming point on the reference leg or rod located within the ligament tunnel femoral and tibial tunnel sections. Which aiming points are opposite to each guide sleeve positioning point along the reference rod. The drill guide arranged to be broken down for removal so as to leave the twist drills in place in the transverse holes.

The transverse hole drilled to intersect the femoral tunnel section will be appropriate to intersect a midpoint of the graft bone end if the mounting is a set screw or cross pin, or at a location that will be across the graft bone where an interference screw is to be used for mounting, and for a soft ligament at approximately a tunnel section mid-point. The first twist drill for use preferably includes markings or indices spaced and numbered therealong that indicate measured distances from the twist drill cutting end. The indices are for use for determining the depth of drill penetration to the femoral and tibial tunnel sections for selection of a length of fastener device, particular for selection of a length of set screw type fastener device. The drill guide is then removed leaving the twist drill or drills in place. A soft tissue guide is fitted over each twist drill, with a soft tissue guide serrated end urged into the patients skin, seating against the bone. Each twist drill is then removed and replaced with a K-wire. The K-wire is used for guiding additional drilling to enlarge the transverse hole, and for guiding a cannulated fastener device turned thereon to intersect, but not extend into, the tunnel section.

Alternatively, the twist drill or drills themselves can be utilized for guiding both additional drilling to enlarge the transverse hole and to serve as a guide whereaalong the cannulated set screw or screw is turned to intersect, but not extend into the tunnel section.

A bone end of the ligament graft is then fitted with a ligament pusher to insert and slide the femoral bone end through the tibial entry and therealong to the end of the femoral tunnel section. A preferred ligament pusher is a K-wire type rod that includes a screw end, with a collar fitted therearound between the rod and screw end. The screw end is turned into the femoral bone end, alongside the tendon, to where further turning is blocked by the collar. The femoral bone end, mounted onto the screw end, is then fitted into and urged along the ligament tunnel to where it butts into the femoral section end, and the screw end is then turned out of the femoral bone end and slid back along the ligament tunnel, alongside the tendon and tibial bone end that is located in the tibial tunnel section. The fastener device is then turned into the femoral tunnel section to engage and mount the bone end therein. Which fastener device may be a cannulated set screw that is turned into the side of the bone end, wedging the opposite bone end side against the tunnel wall; may be within the scope of this disclosure, a cannulated screw that is turned between the bone end and tunnel wall, blocking withdrawal of the bone end as an interference screw; or may be a cross pin that is fitted through the bone end and into the opposite tunnel wall, locking the bone end in place in the femoral tunnel section. Additionally, for providing added purchase, a cross pin having a diameter that approximates a K-wire, is guided through the longitudinal center passage of the cannulated set screw, through the bone end, and into the opposite tunnel section wall.

The set screw and cross pin fastener device combination or a cross pin alone can be fitted through a loop of a semitendinosus, soft tissue graft, the graft draped thereover, with the ligament graft ends then pulled from and secure at the tibial tunnel end. As an another mounting arrangement for maintaining a semitendinosus, soft tissue graft, in the femoral tunnel section, the cannulated set screw is turned to the femoral tunnel section and a cleated washer mounted is fitted onto the set screw end. The set screw is then turned into the femoral tunnel section, the washer cleats engaging the graft side and urging it against the tunnel wall, securely mounting the ligament therein.

With the femoral bone end of the ligament graft mounted, as set out above, in the ligament tunnel femoral section, the tibial bone end, that is maintained under tension, is mounted in the tibial tunnel. This mounting can be by a turning of an interference screw between the bone end and tunnel wall. Or, where a set screw, cross interference screw or cross pin type mounting is desired, prior to fitting the ligament graft in the ligament tunnel, the preferred drill guide can be used, as described above, to also form a transverse hole into the tibia that intersects the tibial tunnel section and using the soft tissue guide and K-wire, as set out above, a surgeon can turn a cannulated set screw or cannulated screw along the K-wire into the tibial bone end of the ligament graft, as a set, interference or cross pin mounting. For the semitendinosus, soft tissue graft, the graft ends can be secured to the tibial cortex adjacent to the tunnel end, as by a staple or other appropriate fastener device.

BRIEF DESCRIPTION OF THE DRAWINGS

These and other objects and features of the present invention in a cross pin and set screw femoral and tibial fixation apparatus and method will become more fully apparent from the following description in which the invention is described in detail in conjunction with the accompanying drawings.

FIG. 6 is a view like FIG. 5 after the K-wire has been removed and replaced with a cannulated set screw;

FIG. 6A is a sectional view taken within the line 6A—6A of FIG. 6 showing the cannulated set screw rear driver end;

FIG. 6B is view like FIG. 5 only showing a cannulated screw as a cross pin as having been substituted for the cannulated set screw;

DETAILED DESCRIPTION

The invention is for a practice of an arthroscopic surgical procedure for replacement of a knee cruciate ligament that involves the fixation of the ligament ends in the prepared tunnel. The method and apparatus for its practice of the invention provides an efficient ligament mounting technique that is particularly suited for mounting a bone tendon bone type ligament graft, as well as a semitendinosus ligament graft, in femoral and tibial tunnel sections of a straight ligament tunnel. The invention preferably involves a utilization of a drill guide, like that set out as a Multiple Guide sleeve Drill Guide, U.S. patent application Ser. No. 07/930/273. In a use of such drill guide, it has been a problem for a surgeon to maintain or relocate the transverse hole after removal of a twist drill that is turned to the ligament tunnel for guiding additional items including a fastener device, therein. Particularly this is true if such items or fastener device is not immediately fitted into the prepared transverse hole after the twist drill and drill guide have been removed. The present invention solves this problem by providing a method and apparatus to where a transverse hole or holes formed to intersect a section or sections or a straight ligament tunnel 15 remain available to the surgeon.

In one embodiment, the surgeon after forming the transverse hole, prior to withdrawal of the twist drill, fits a soft tissue guide thereover prior to drill removal followed a succession of a K-wire and larger diameter second twist drill followed by a fastener device. A second embodiment includes leaving the first twist drill in place that is then used as a guide for passing the larger diameter second twist drill followed by the fastener device therealong. Both procedures for insuring that the transverse hole remains open and available to the surgeon during a ligament replacement procedure. Which procedure can also include drilling with a second twist drill a tibial transverse hole to intersect a tibial tunnel section 17, as set out below.

Figures 1, 1A:
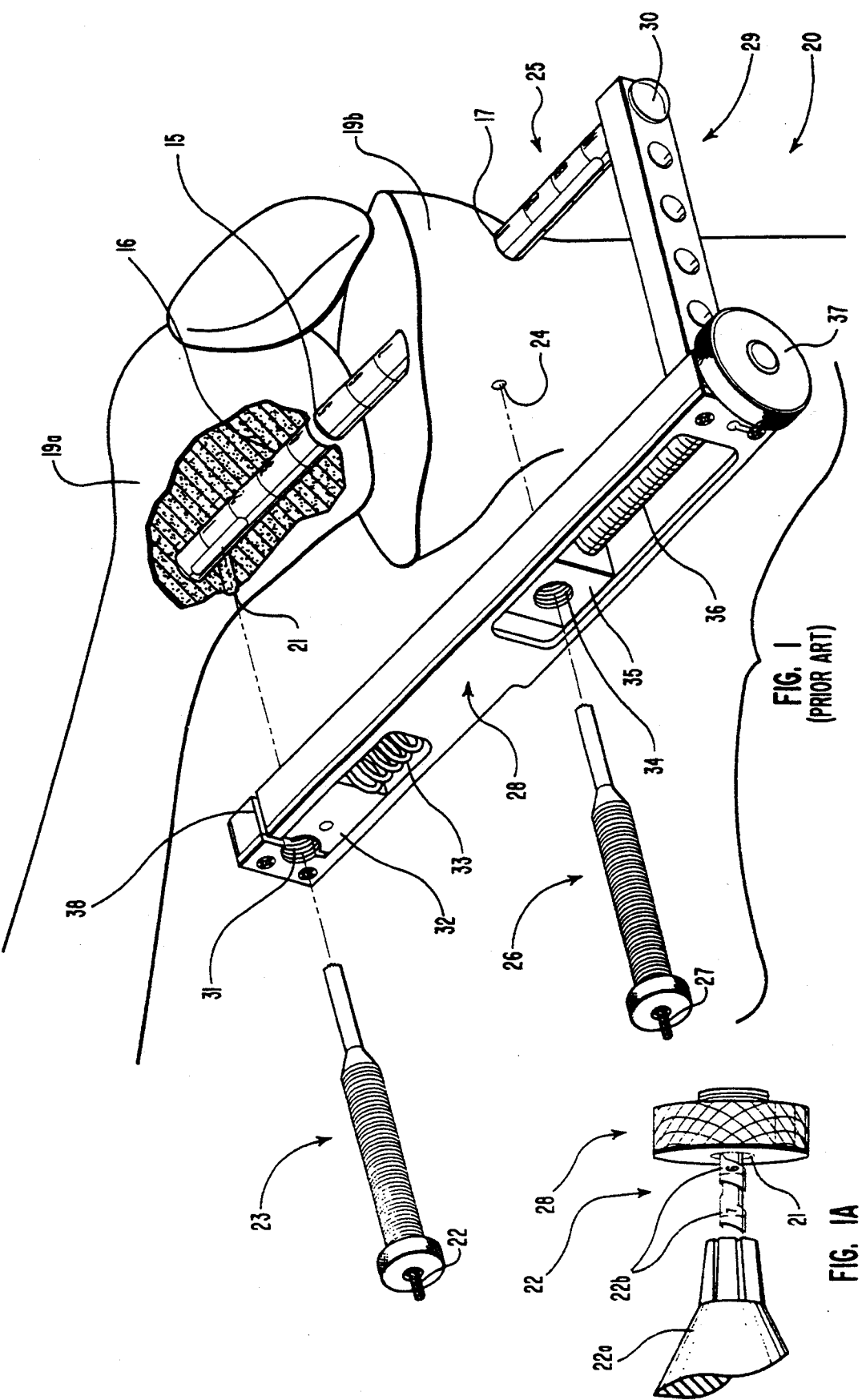
FIG. 1 is a side elevation view of a patient's knee, less the covering skin, showing a drill guide reference leg fitted into a straight ligament tunnel formed therein, and showing a twist drill turned through a guide sleeve of the drill guide, from the medial side, forming a transverse hole that intersects a femoral tunnel section, shown in a broken away section, showing, in broken lines, the drill guide pivoted across the knee to function from the lateral side, and showing, in broken lines, a second guide sleeve turned through a tibial guide sleeve for drilling with a twist drill a tibial transverse hole that intersects the tibial tunnel section.
FIG. 1A is a side elevation view of a drill having spaced indices scribed thereon that is fitted in a chuck for turning in a guide rod of FIG. 1.
Figure 2:
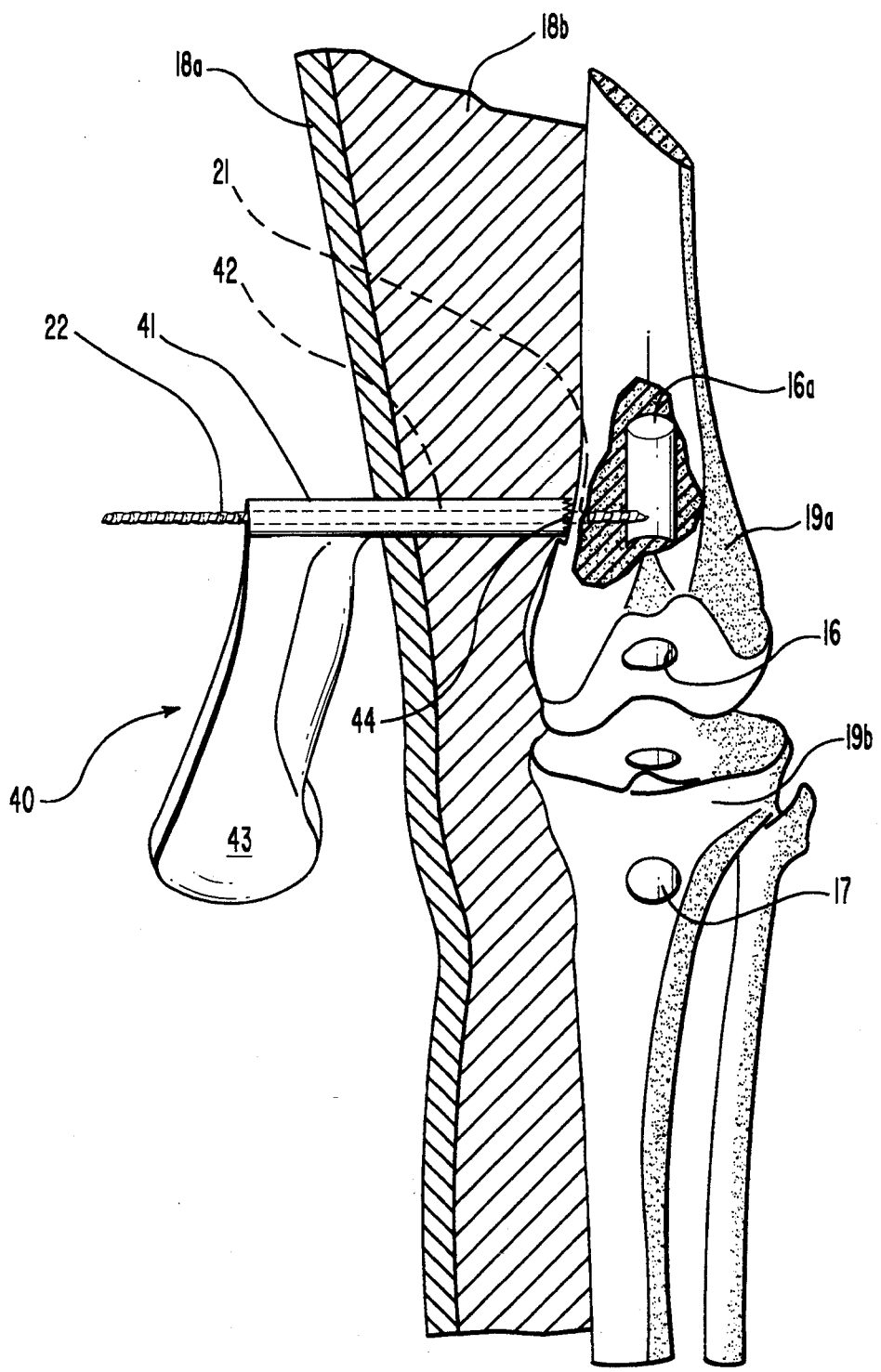
FIG. 2 shows the patients' knee of FIG. 1, including the covering skin, after the drill guide has been removed and showing a soft tissue guide as having been fitted over the twist drill and through the patient's skin to engage the side of their femur.

In practice, a femoral transverse hole 21 is formed utilizing a drill guide 20, that, as set out above and as shown in FIG. 1, is preferably a drill guide like or having the capabilities of a Multiple Guide Sleeve Drill Guide that the inventor is co-inventor of. Drill guide 20 allows for drilling, as by turning a first femoral twist drill 22 and a first tibial twist drill 27, as required, by an electric drill 22a, or the like, to form both the femoral and tibial transverse holes, 21 and 24, respectively, each to intersect a target on the drill guide 20 reference leg 25. Which drill guide 20 includes removable twist guide sleeves 23 and 26, respectively, that are removable from the drill guide to slide off of the first twist drills. Whereafter, the drill guide is removed leaving first femoral and tibial twist drills 22 and 27, respectively, in place. The twist drill 22, and optionally twist drill 27, then serve, in a practice of a first embodiment of the method of the invention, to guide positioning of a soft tissue guide 40 that is fitted thereover, as shown in FIG. 2, and engages the side of the distal femur or proximal tibia, as discussed below.

In practice, as shown in FIG. 1, the drill guide 20 can be utilized to drill femoral transverse hole 21 only, and can also, during the same step in the procedure, be used to drill tibial transverse hole 24. The preferred drill guide 20 includes a guide leg or rod 28, and web member 29 that connects between the guide rod and reference rod or leg 25, forming a U shaped member. The web member 29 and reference leg 25 connection is preferably releasable by turning of a screw 30 through the web member, proximate to its end and into the reference leg 25 end, providing a releasable mounting. With the drill guide reference leg 25 installed in the ligament tunnel 15, a femoral guide sleeve 23 is fitted into a threaded guide sleeve hole 31 of the guide rod 28 for guiding turning of twist drill 22 to form the femoral transverse hole 21. The guide sleeve hole 31 includes, as a hole lower segment a block 32 that is biased by a spring 33. The block 32 is movable to allow the drill guide 23 to be slid therein, with the guide sleeve threads sliding over the threads of the guide sleeve hole 31, with the block 32 urged by spring 33 to engage the guide sleeve threads. Whereafter, it is manually turned by a surgeon into engagement with the patient's knee. Optionally, where it is desired to provide a set screw type mounting of the tibial end of a ligament graft that is under tension in the tibial tunnel section 17, the drill guide 20 can be used to form a transverse hole to the tibial tunnel section. For which use, a tibial guide sleeve 26 can be turned into a threaded hole 34 formed through a sliding block 35, the position of which sliding block along the guide rod 28 is adjustable relative to the guide sleeve hole 31. Sliding block positioning is provided by turning a threaded rod 36 by a surgeon operator who turns a broad head 37 end of the threaded rod. The drilling of the respective femoral and tibial transverse holes 21 and 24, it should be understood, can be undertaken, as shown, from the medial side of the patient's knee, or the drill guide 20 can be pivoted across the knee to the lateral side, as illustrated by the partial broken line section of the drill guide web member 29.

After drilling the respective femoral and tibial transverse holes 21 and 24, the respective first twist drills 22 and 27 are left in place. The block 32 can then be displaced away from the guide sleeve 23 that can then be slid out of guide sleeve hole 31, leaving the twist drill 22 therein. The twist drill 22 can the be passed through a slot 38 that extends through the side of the guide rod and into the guide sleeve hole 31, releasing the drill guide 20 from the twist drill 22. Where a tibial transverse hole 24 is not drilled, with the tibial ligament end to be otherwise secured in the tibial tunnel section 17, the above releases the drill guide from the twist drill 22. Thereafter, the drill guide reference leg 25 can be pulled out from the ligament tunnel 15, leaving the twist drill 22 in the femoral transverse hole 21, as shown in FIG. 2, ready to receive a soft tissue guide 40 that is fitted thereover. Where the tibial transverse hole 24 is formed, as described, utilizing twist drill 27, to remove the drill guide 20 from the twist drill 27 the drill guide web member 29 is released from its connection to the reference leg 25 by turning the screw 30 out of engagement therewith. The connected web member 29 is thereby released from the guide rod 28, allowing the guide sleeve 26 that is maintained in the guide rod sliding block 35 to be pulled off from the twist drill 27. Which tibial twist drill 27 can then also receive, in a practice of a first embodiment of the invention, a soft tissue guide 40 fitted thereover, as described in FIG. 2, with respect to the femoral twist drill 22. The tibial transverse hole 24 is processed to receive a fastener device, as described below for, with respect to a discussion of the enlargement of the femoral transverse hole 21.

A first step in the femoral transverse hole 21 processing is illustrated in FIG. 1A that shows indices 22b scribed thereon at spaced intervals as (6) and (7) respectively, that reflect measured distances along the drill. The indices 22b are for alignment with the face of the guide rod 28 for a surgeon to determine, by the guide rod face alignment with one of the indices, depth of first twist drill penetration. This measurement is useful, as set out in detail below, for selection of an appropriate length of fastener device, particularly a set screw, for mounting ligament ends in the respective femoral and tibial tunnel sections 16 and 17.

FIG. 2 shows the drill guide 20 as having been removed, and illustrates a practice of the first embodiment of the method of the invention, with the soft tissue guide 40 fitted over twist drill 22. With a tibial transverse hole formed, as described above, a like soft tissue guide 40 will be employed to maintain the location of which tibial transverse hole also. Accordingly, a description of the preparation of the femoral transverse hole 21 to receive a fastener device, and the fitting of a fastener device therein, should be taken as the same for a tibial transverse hole preparation and use.

FIG. 2 shows the preferred soft tissue guide 40 as including a barrel 41 that has a center longitudinal passage 42, shown in broken lines, formed therethrough that is to slide over twist drill 22. The barrel 41 is mounted onto a pistol grip 43 that is held by a surgeon who urges a barrel forward end into the skin 18a and tissue 18b of a patients knee to a side of a proximal femur 19a, shown as a medial side. To aid in which barrel 41 insertion the barrel forward end is serrated at 44 to provide for cutting, when urged, through the skin and tissue and biting into the bone cortex surrounding the femoral transverse hole 21.

Figure 3:
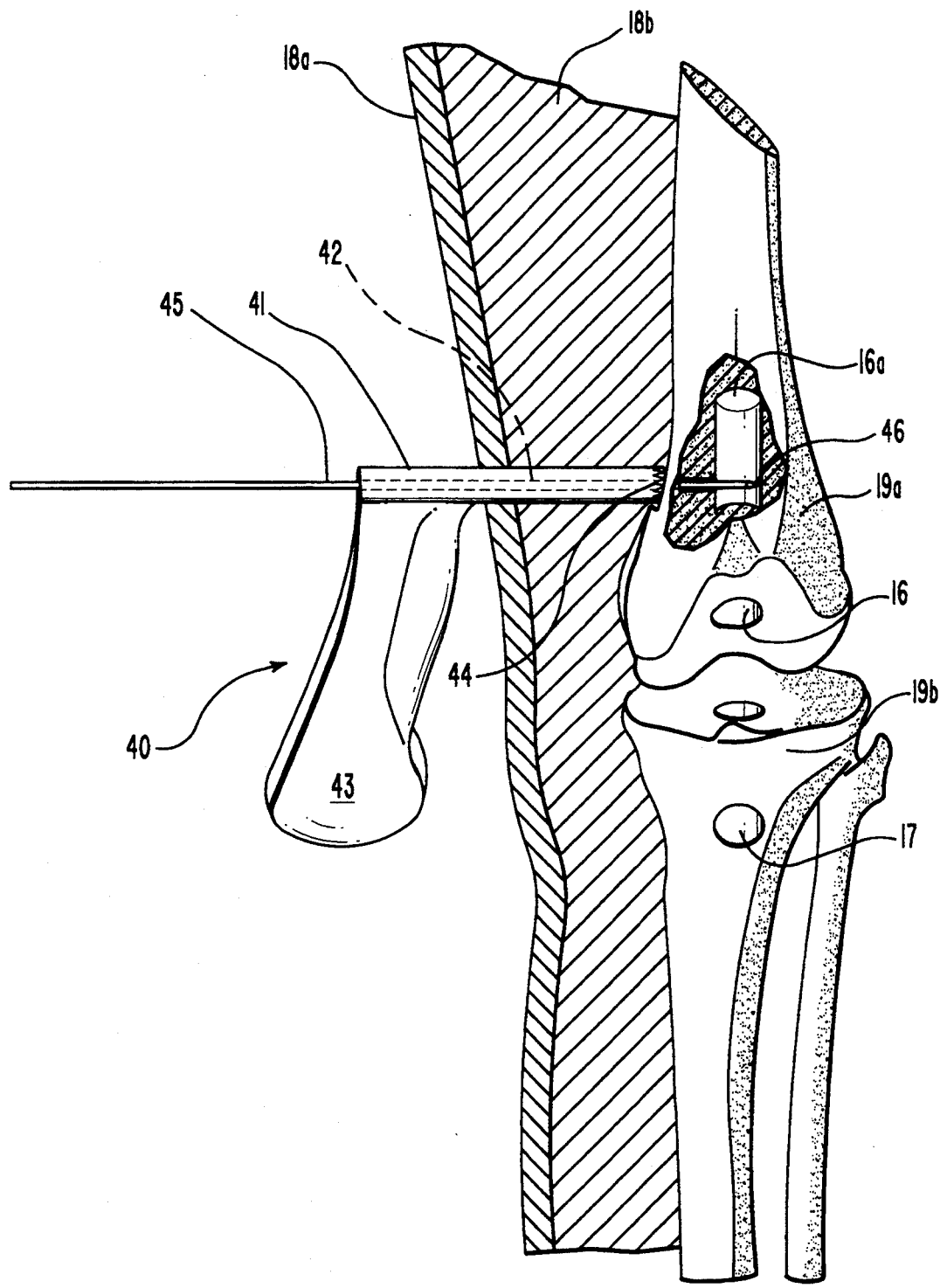
FIG. 3 is a view like that of FIG. 2 only showing the drill as having been removed and replaced with a K-wire.

After seating the barrel 41 serrations 44 into the femur 19a cortex, as shown in FIG. 2, a surgeon maintains that seating and pulls the twist drill 22 out through the barrel 41 hole 42. He/She then replaces the twist drill with a K-wire 45, as shown in FIG. 3. The K-wire 45, preferably has a pointed forward end 46 that is fitted into the femoral transverse hole 21, replacing twist drill 22. The K-wire serves as a guide along which additional apparatus of the invention are moved in a practice of the first embodiment of the method of the invention.

An alternate or second embodiment of a practice of the method of the invention, as set out hereinbelow with respect to a discussion of FIGS. 4A and 5A, involves leaving the first twist drill or drills 22 and 27 in place after removal of drill guide 20. The first twist drills then guide the second cannulated twist drill 47 and the fastener device fitted and turned, the first twist drill or drills functioning like the K-wire 45.

Figure 4:
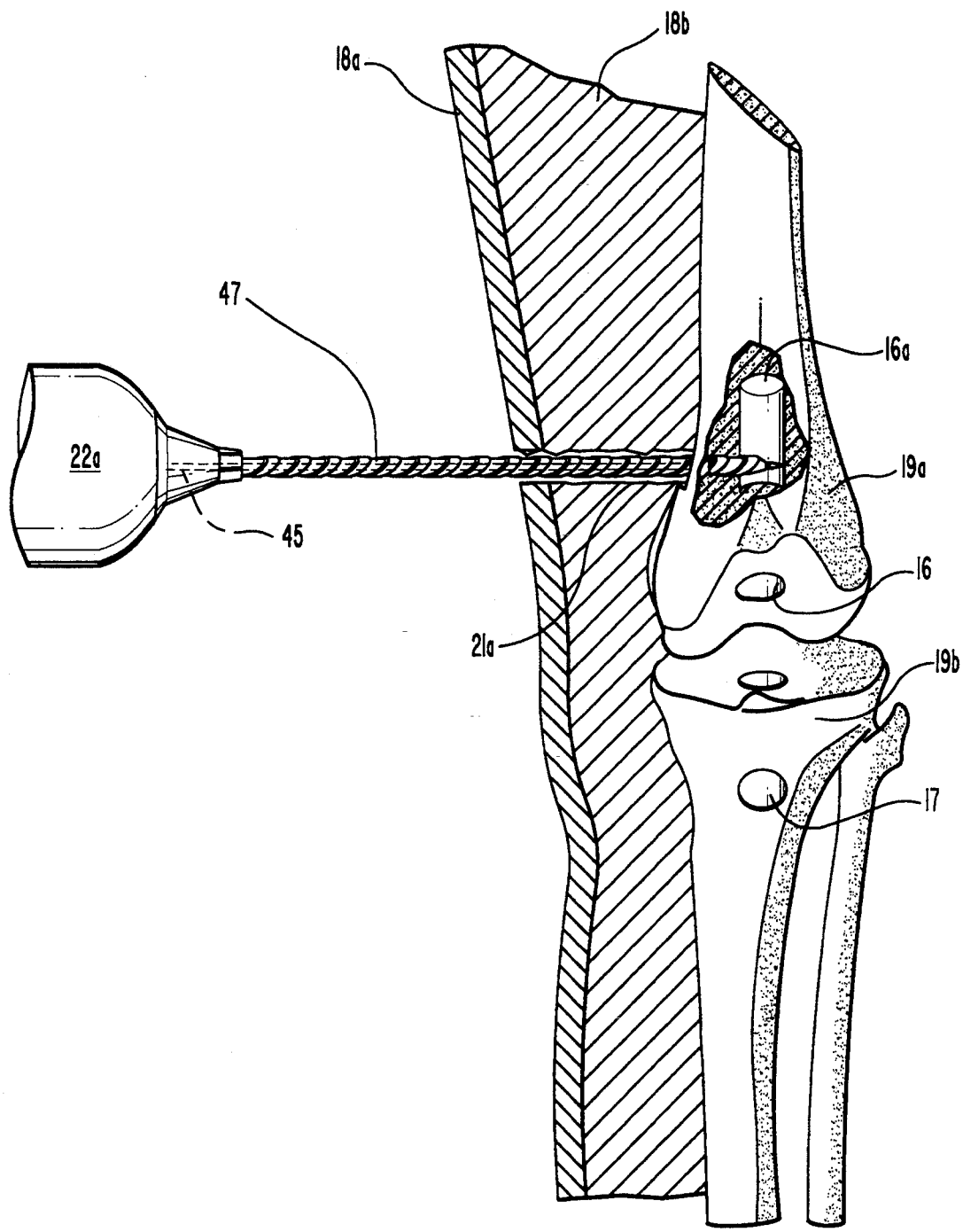
FIG. 4 is a view like that of FIG. 3 after the soft tissue guide has been removed and showing a cannulated twist drill turned along the K-wire for enlarging the transverse hole to the femoral tunnel section of the ligament tunnel.
Figure 4A:
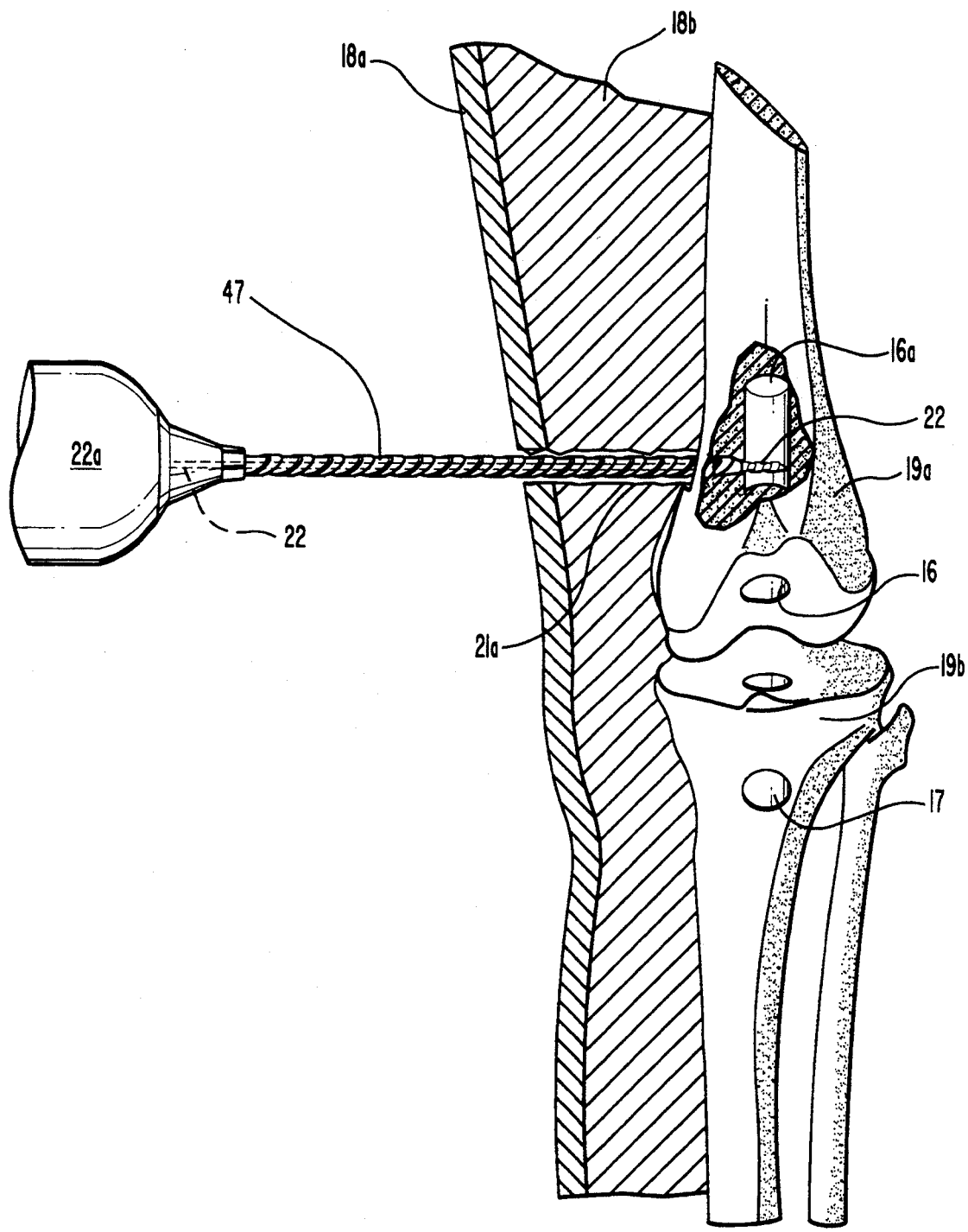
FIG. 4A is a view like that of FIG. 1 after the drill guide has been removed leaving the first twist drill in place that is shown being used as a guide for receiving the cannulated twist drill turned therealong.

A further practice of the first embodiment of the method of the invention is shown in FIG. 4 as involving drilling out of the femoral transverse hole 21 to form an enlarged transverse hole 21a. This is done by an electric drill 22a, or the like, that turns a cannulated twist drill 47, that is guided along the K-wire 45, to form the enlarged transverse hole 21a. With FIG. 4A illustrating a practice of the second embodiment of the method of the invention wherein the first twist drill 22 is shown as guiding the cannulated twist drill 47 therealong to form the enlarged transverse hole 21a.

Figure 5:
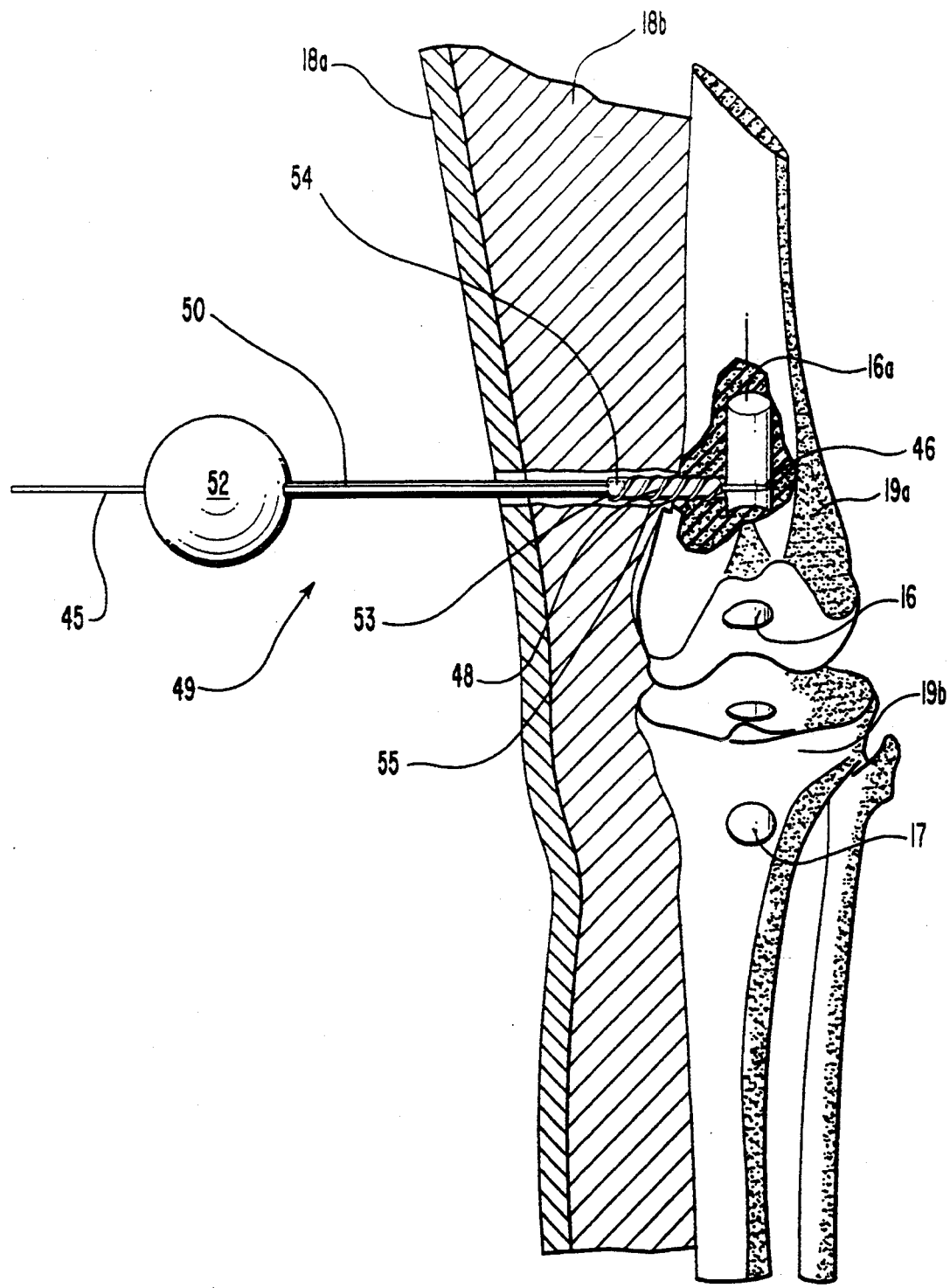
FIG. 5 is a view like that of FIG. 4 after the cannulated twist drill has been removed and showing a cannulated set screw being turned by a driver along the K-wire into the transverse hole to the side of the femoral tunnel section of the ligament tunnel.

FIG. 5 shows the patient's leg of FIGS. 1 through 4 with the cannulated drill 47 pulled off of the K-wire 45 and replaced with a cannulated set screw 48. The cannulated set screw is shown mounted onto a forward end of a turning tool 49, The turning tool 49 includes a barrel 50 that has a longitudinal center opening 51 formed therethrough, as shown in broken lines, and mounts a ball 52 on its rear end as a hand grip. The ball 52 is preferred as a hand grip, though other grips could be used within the scope of this disclosure, for gripping and turning by an operator to turn the barrel 50. The set screw 48 receives a coupling end 53 of the barrel that is fitted into a set screw rear end recess 54, mounting the set screw thereto. The turning tool 49 and cannulated set screw 48 are guided along the K-wire, with the cannulated set screw threads 55 turning into and seating in the enlarged transverse hole 21a. Which turning of the set screw 48 is to where a screw blunt end 56 just enters to align with the femoral tunnel section 16 wall. FIG. 5A is the same as FIG. 5 except that the first twist drill 22 is shown as having been left in place to serve the function described for K-wire 45.

Figure 5A:
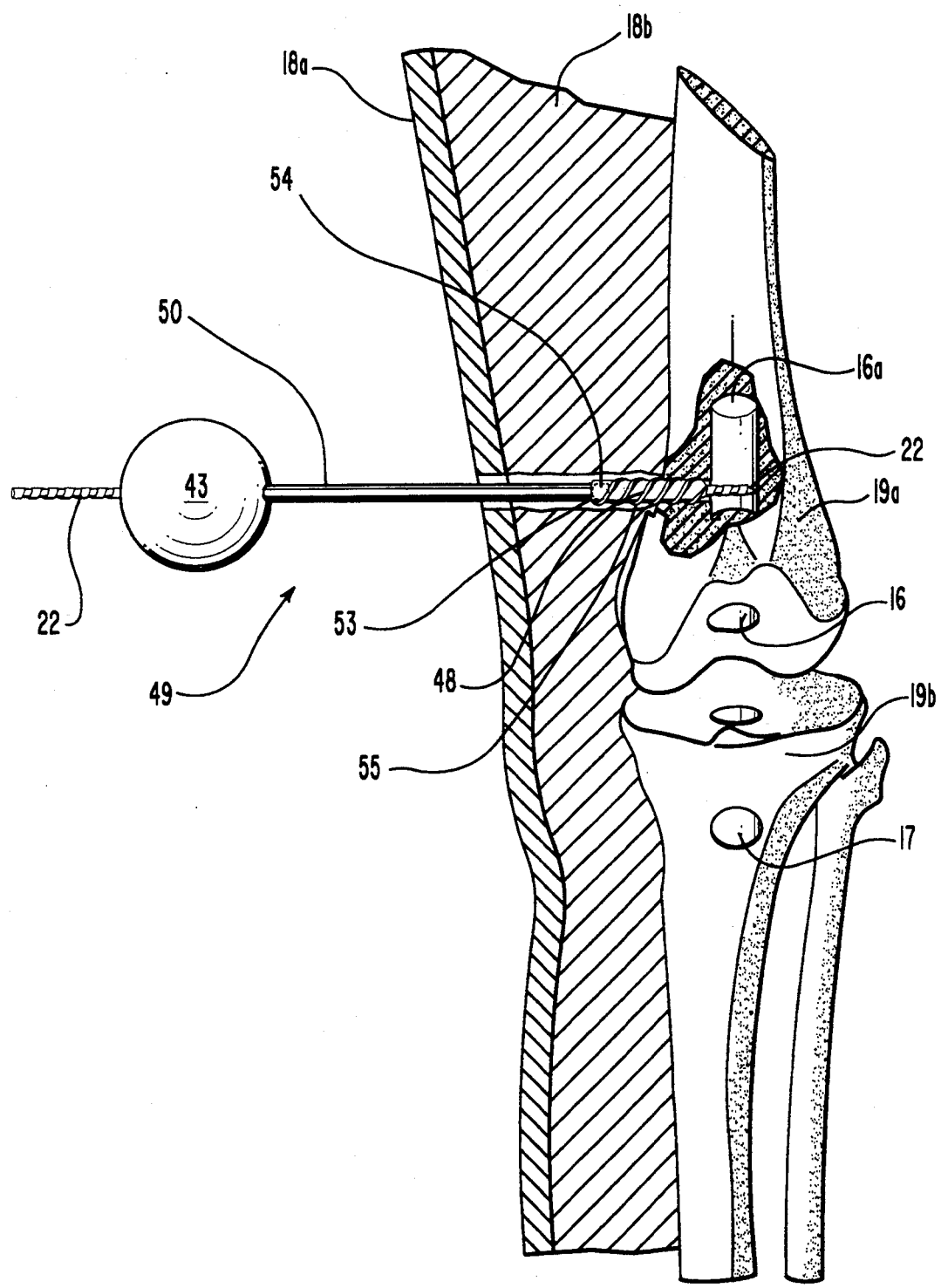
FIG. 5A is a view like FIG. 5 only showing the cannulated set screw as being turned along the first twist drill.

FIG. 6 shows the patient's leg and the turning tool 49 that mounts the cannulated set screw of FIG. 5, with the K-wire 45, or the first twist drill 22 of FIG. 5A, pulled therefrom, leaving the turning tool coupling end 53 seated in the set screw rear end recess 54. FIG. 6A is an end sectional view of the turning tool end 53 fitted into the set screw rear end recess 54, showing the tool end and recess as having opposing engaging surfaces, each shown herein as having a hexagon cross section. Though, of course, other sided configurations, such as a square, triangle, or the like, as would be suitable for transferring turning of the barrel 50 into turning of the set screw 48 could be so employed.

FIG. 6B is an enlarged view of the distal femur 19a of FIG. 6 showing the femoral tunnel section 16 formed therein, and showing the enlarged transverse hole 21a as intersecting the femoral tunnel section. In FIG. 6B the cannulated set screw 48 is shown as having been replaced with a cannulated screw 57 that has a pointed forward end 58. The screw 57 includes spaced apart threads 59 that are like the threads 55 of the cannulated set screw 48 and extend outwardly from around the screw body from the forward or pointed end 58 to a blunt rear end 60. Which blunt rear end is like the coupling end 54 of the cannulated set screw 48. While the cannulated screw rear end 60 is preferably like coupling end 54, it may be a similar coupling arrangement, and, within the scope of this disclosure, may be a coupling end like the coupling end 53 of the turning tool 49, as described above. So arranged, the turning tool 49 is for turning the cannulated screw 57 into the enlarged transverse hole 21a, and across the femoral tunnel section 16, with the cannulated screw 57 thereby passed through the end of a ligament graft that is positioned in the femoral tunnel section 16. In such ligament mounting, as discussed below, the cannulated screw 57 functions as a cross pin for endosteally mounting the femoral end of a ligament graft in that femoral tunnel section.

Figure 6C:
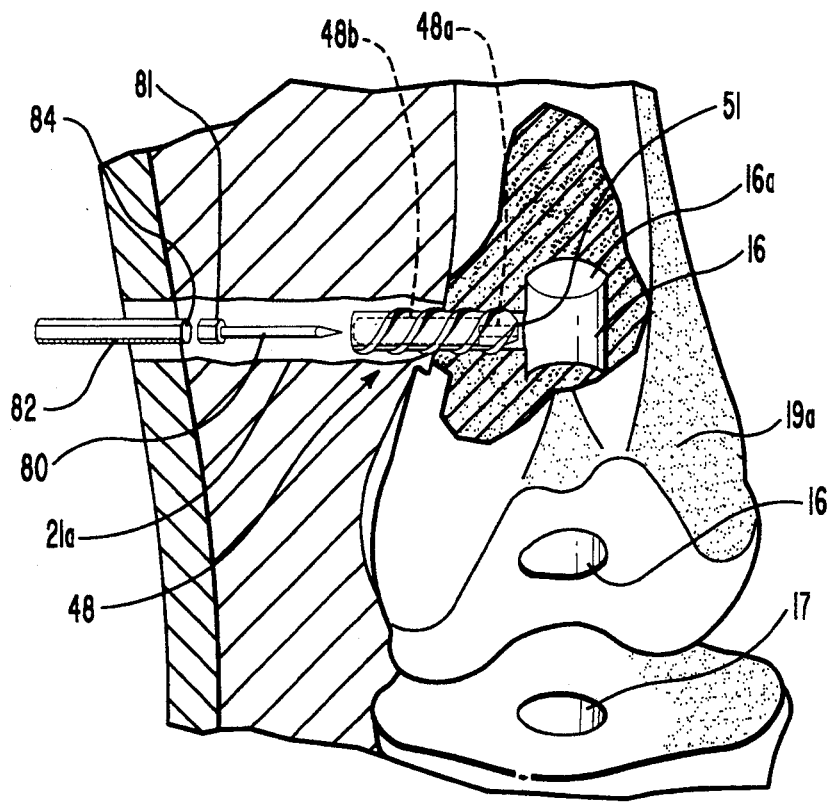
FIG. 6C is a view like FIG. 6 only showing the cannulated set screw seated in the transverse hole and showing the driver end aligned with a coupling end of a cross pin that is aligned with the passage through the cannulated set screw.
Figure 6D:
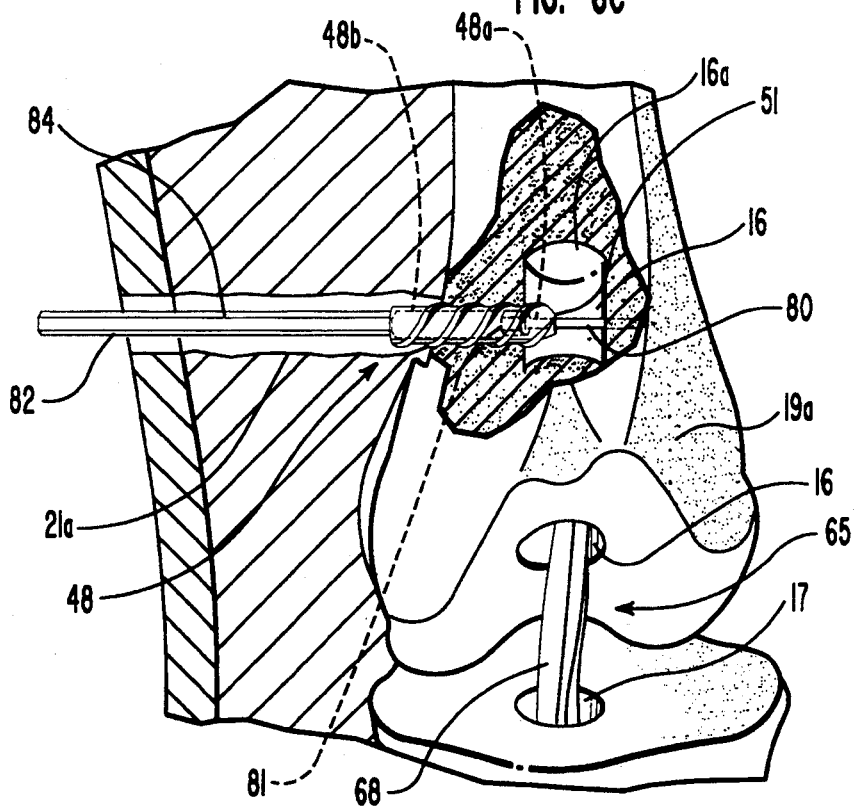
FIG. 6D is a view like FIG. 6C only showing the cannulated set screw as having been turned into the femoral tunnel section and the cross pin as extending from the set screw nose end across the femoral tunnel section.

FIG. 6C shows the cannulated set screw 48 seated at the end of the enlarged transverse hole 21a, the set screw blunt end 56 shown as just entering the femoral tunnel section 16a. A cross pin insert 80 is shown aligned for fitting into the set screw longitudinal passage 48a that is enlarged into a sided coupling end 48b, shown in broken lines. The cross pin insert 80 is to be urged through the cannulated set screw and across the femoral tunnel section to pass through a ligament graft therein. To control installation, the cross pin insert 80 includes a coupling end 81 that is a sides cylinder 82 of a cross section to fit within the sided coupling end 48b that is formed longitudinally in the set screw rear end, and includes a center longitudinal cavity that is preferably sided for receiving a turning end 84 of a turning tool that is like the turning tool 49. The turning end 84 to fit within the cavity to both mount the cross pin insert for guiding a cross pin pointed end 85 into the set screw longitudinal passage 48a, and for turning the cross pin coupling end 81 in its mounting in the set screw coupling end recess 48b, turning the set screw 48 also. Shown in FIG. 6D, with the cross pin insert 80 fully inserted into the set screw 48 it extends from the set screw nose end 56 into the femoral tunnel section. Turning the driver turning end 84 thereafter turns both the set screw 48 and cross pin insert to the attitude shown in FIG. 6D where both a cross pin and set screw mounting of the femoral bone end 66 of the bone tendon bone ligament graft 65 is provided, providing an exceptionally strong purchase. Should thereafter it become necessary to release the ligament graft end mounting, the turning tool can be reinserted into the enlarged transverse hole 21a and into the cross pin insert coupling end 81, and the turning tool is then turned to back the set screw and cross pin insert out of the femoral tunnel section, releasing the ligament graft.

Figures 7, 7A:
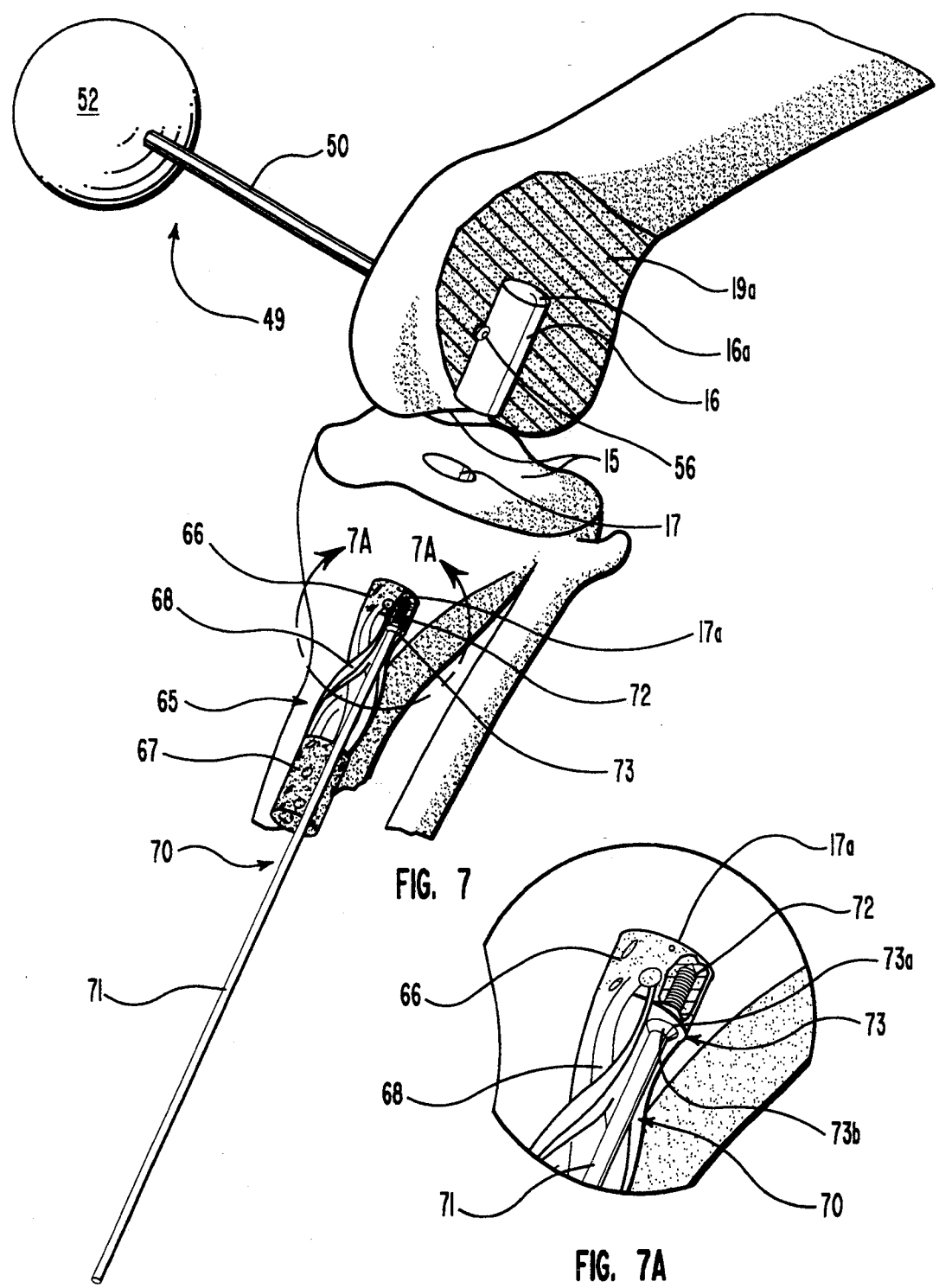
FIG. 7 is a lateral side elevation view of the patient's knee, less the covering skin, showing the set screw arrangement of FIG. 6 and showing a ligament pusher of the invention turned into a bottom surface of a femoral bone end of a bone tendon bone type ligament graft that urges the femoral bone end into and along the ligament tunnel.
FIG. 7A shows an enlarged side elevation view of the ligament pusher of FIG. 7 that is shown as a K-wire type rod with a screw end and as including an outstanding collar between the screw end and rod.

FIG. 7 shows the patient's knee of FIGS. 1 through 6 rotated towards the lateral side to better show the fitting of one type ligament graft 65 into the open tibial tunnel section end 17a. The ligament graft 65 is shown as a combination of femoral and tibial bone ends 66 and 67, respectively, with a section of a ligament material 68 shown secured therebetween. A common name for which ligament graft 65 is a bone tendon bone ligament graft. The first embodiment of the apparatus and the method of the invention, as set out above, are preferably utilized to provide for mounting a ligament graft like the bone tendon bone graft 65 in the ligament tunnel 15. Additionally, it should be understood, the invention, as set out below with respect to a discussion of FIGS. 7B, 7C, 12 and 12A, is also appropriate for use for mounting a semitendinosus or soft tissue ligament graft, within the femoral tunnel section.

Shown in FIGS. 7 and 7A, for installing the femoral bone end 66 of ligament graft 65, a ligament pusher 70 is provided that consists of a straight wire 71 that includes a pointed screw 72 secured onto an end thereof, with a round collar 73 maintained around the base of the pointed screw. The pointed screw 72 end is for turning, as shown in FIG. 7 and best in FIG. 7A, into a base or bottom surface of the femoral bone 66 to where that bone end rests upon a flat top surface 73a of the collar 73. The femoral bone end is thereby mounted onto the upper end of the wire 71 that extends alongside the ligament material 68 and past tibial bone end 67.

Figure 8:
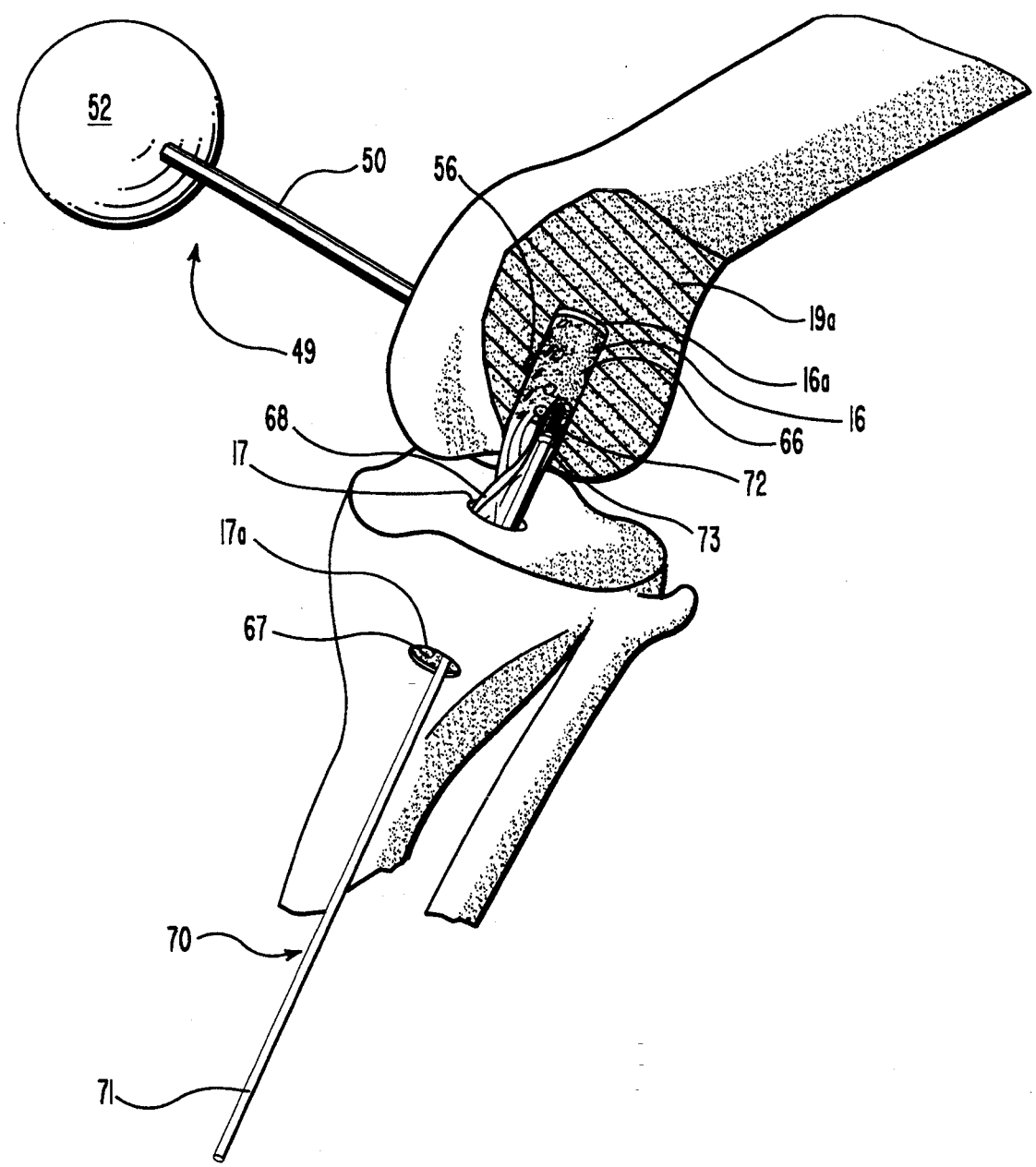
FIG. 8 is a view like that of FIG. 7 showing the ligament graft femoral bone end fully inserted into the femoral section of the ligament tunnel with the tibial bone end of which ligament graft shown installed in the tibial tunnel section.

Shown in FIGS. 7 and 7A, the ligament graft femoral bone end 66 mounted to the ligament pusher 70 is inserted into the open end 17a of the tibial tunnel section 17 and urged therealong by an operator manipulating the wire 71 to where the top surface of the femoral bone end 66 contacts the top surface 16a of the femoral tunnel section 16, as shown in FIG. 8. In which passage the femoral bone end 66 travels to a position alongside the cannulated set screw 48 end 56 that is thereby aligned with a approximately a mid-point of the femoral bone end. So arranged, as shown in FIG. 8, further turning of the turning tool 49 turns the set screw into engagement with the femoral bone end 66, preliminarily seating it in the femoral tunnel section 16. The ligament pusher screw end 72 is then turned out of engagement with the bottom surface of the femoral bone end and the ligament pusher 70 is pulled out of the ligament tunnel 15, traveling alongside the ligament graft 68 and tibial bone end 67. In which travel, the collar 73 sloping surface 73b, as shown best in FIG. 7A, tends to lift over and slip along the side of the tibial bone end 67, prohibiting binding thereagainst. The preliminary endosteal seating of the femoral bone end in the femoral tunnel section 16 maintains the ligament graft positioning as the ligament pusher 70 is removed.

Figure 9:
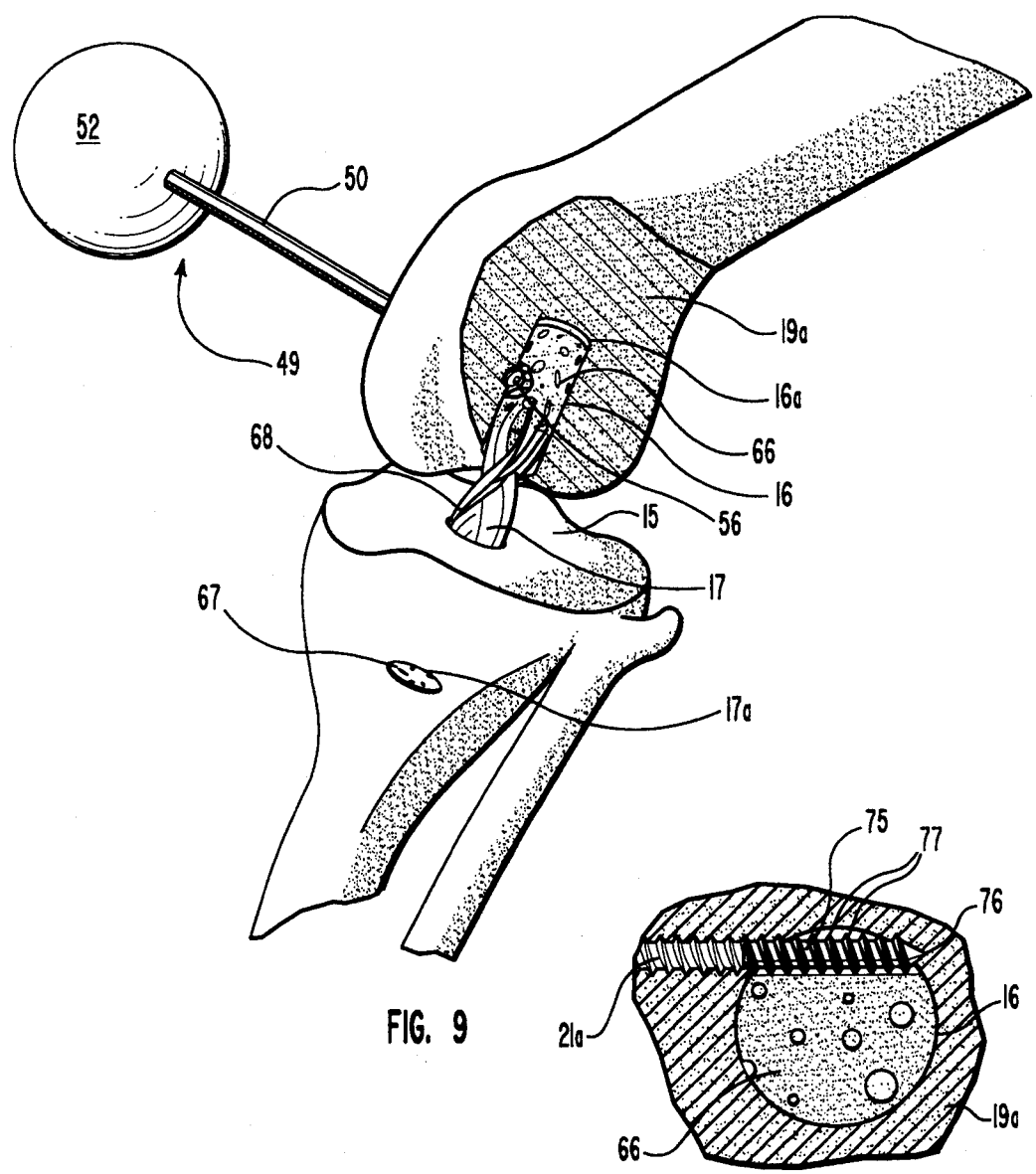
FIG. 9 is a view like that of FIG. 8 showing the set screw as having been turned by the driver into engagement with the side of the femoral bone end.

With the femoral bone end 66 seated, as set out above, in the femoral tunnel section 16 the cannulated set screw end 56 is turned against the side of the femoral bone end 66, as shown in FIG. 9. The cannulated set screw end 56 thereby bows the bone end away from the set screw contact, as illustrated in FIG. 9 at a cut away section of femoral bone end 66, the opposite femoral bone end surface thereby engaging and binding against the side of the femoral tunnel section 16. An endosteal mounting of the femoral bone end in the femoral tunnel section is thereby provided that is very resistive of being pulled therefrom.

Figures 7B, 7C:
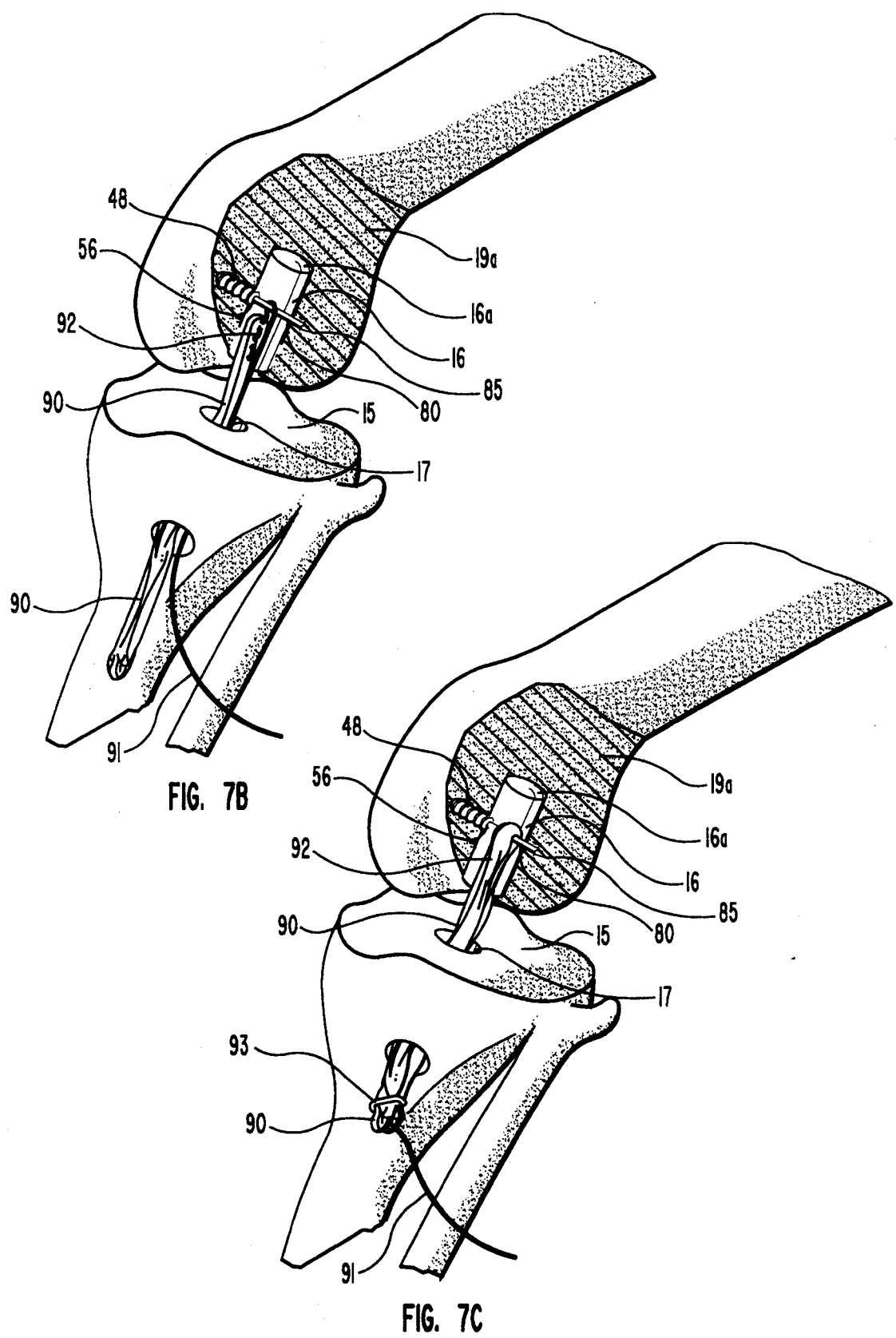
FIG. 7B shows a semitendinosus ligament graft that includes a suture secured to one end that is formed into a loop and fitted into the femoral tunnel section with a cross pin shown fitted through the suture loop and into the opposite tunnel side.
FIG. 7C is a view like that of FIG. 7B only showing the suture as having been pulled out from the tibial end of the straight ligament tunnel and showing the ligament graft ends having been aligned and a staple fitted thereover and driven into the tibia cortex.

FIGS. 7B and 7C show a utilization of a cross pin for mounting a semitendinosus (soft tissue) ligament graft 90 in the femoral tunnel section 16 to near the tunnel section top end 16a. This ligament mounting procedure involves a guiding of a cross pin, like the cross pin insert 80 of FIGS. 6C and 6D, across the femoral tunnel section and through a loop formed in a suture 91 that is secured to the ligament graft 90 end 92. The cross pin pointed end 95 is to pass through the loop and into the opposite tunnel wall, supporting the ligament graft 90 as a cross pin mounting. Whereafter, the suture 91 can be pulled out from the tibial tunnel section end, as shown best in FIG. 7C, to where the ligament graft ends overlay one another. With a tensile force applied thereto, a staple 93 can be positioned thereacross and the staple legs driven into the tibia cortex, securing the ligament ends under tension thereto.

FIGS. 7B and 7C show the cross pin insert 80 of FIGS. 6C and 6C being used as the cross pin for endosteally mounting the ligament graft 90. Cross pin insert 80 is set out above as being guided through the longitudinal center passage 48a of the cannulated set screw 48, projecting outwardly from the nose end 56 to extend across the femoral tunnel section 16. This arrangement, of course, provides a satisfactory cross pin mounting. It should, however, be understood that a cross pin arrangement, such as a K-wire, or the like, can be guided from without the knee as by a drill guide of the invention, as set out hereinabove, to pass through the suture loop, to provide a cross pin mounting, within the scope of this disclosure. Additionally, it should be understood, the ligament graft 90 could itself be formed into a loop for receiving the cross pin fitted therethrough, within the scope of this disclosure. For fitting a ligament graft 90 loop, or the loop in a suture 91 secured to the ligament graft 90, into a straight ligament tunnel to approximately the end 16a of the femoral tunnel section 16, a tendon threader device like that set out in an application for patent, U.S. patent application Ser. No. 07/956,322, is preferred.

Figure 9A:
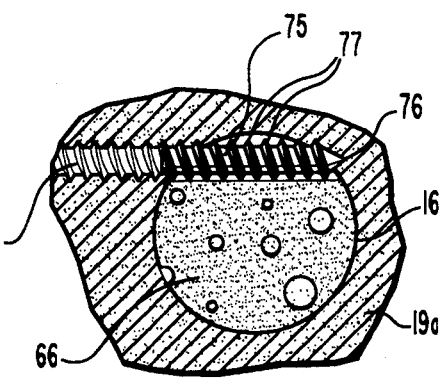
FIG. 9A is an enlarged cross sectional view of the femoral bone end shown fitted in the femoral tunnel and showing a cannulated screw as having been turned across the ligament tunnel contacting the side of the femoral bone end.

An alternative femoral bone end 66 endosteal mounting in the femoral tunnel section 16 is illustrated in FIG. 9A, where a cannulated screw 75 is shown turned across the femoral bone end 66, providing an interference mounting thereof in the femoral tunnel section 16. Which mounting involves turning the cannulated screw 75 through the enlarge transverse hole 21a and across the side of the femoral bone end 66 and the femoral tunnel section 16, endosteally mounting the ligament graft end therein. To form which enlarge transverse hole 21a so as to enable passage off-center to the femoral bone end, across the femoral tunnel section, the drill guide reference leg 25 may be displaced from exact alignment with the guide rod 28, thereby altering the target point on which reference leg to a side of the femoral tunnel section. Or, alternatively, a flat or flattened portion of the femoral bone end 66 can be positioned in alignment with the enlarged transverse hole 21a such that the cannulated screw 75 will turn through the space between which flat or flattened portion of the bone end and the femoral tunnel section wall. So arranged, the cannulated screw 75 is selected such that, when turned therein, it will have a diameter that is sufficient to span the open area to provide a secure interference mounting between the femoral bone end 66 and the femoral tunnel section 16 wall.

Figure 10:
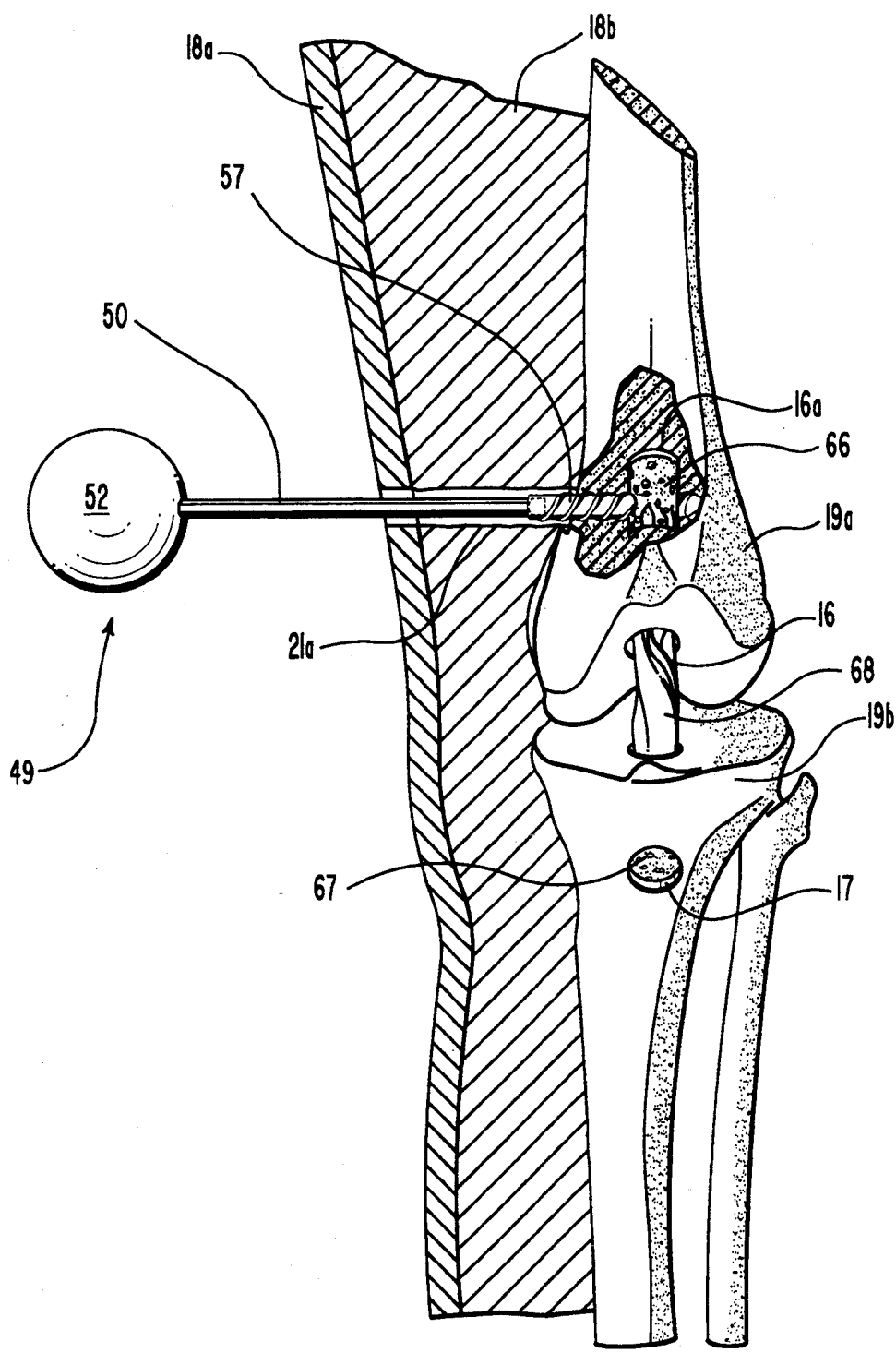
FIG. 10 is a front view of the patients knee of FIG. 9 showing the cannulated set screw as having been turned against the femoral bone end, and showing, in broken lines, a screw that has been turned through the femoral bone end and into the opposite ligament tunnel side as a cross pin.

FIG. 10 shows still another arrangement for endosteally mounting the ligament graft femoral bone end 66 in the femoral tunnel section 16. This embodiment preferably includes the cannulated screw 57, that has been described hereinabove with respect to FIG. 6B. The cannulated screw 57 is turned, utilizing turning tool 49, across the femoral tunnel section 16, so as to pass through the femoral bone end 66, functioning as a cross pin mounting that extends between the femoral tunnel section walls.

Figure 11:
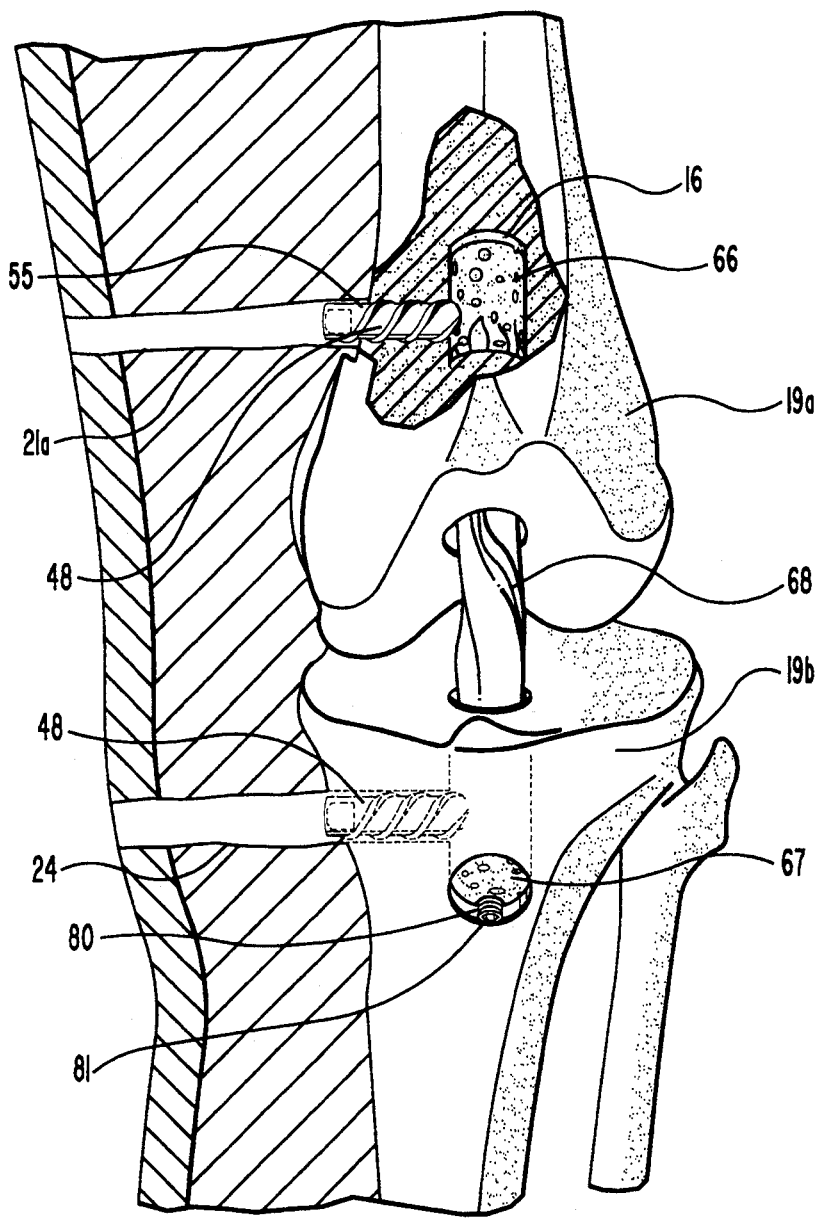
FIG. 11 shows the cannulated set screw of FIG. 10 turned into the femoral bone end so as to leave a rear end of which set screw slightly above the femur cortex, and showing, in broken lines, as an alternative tibial bone end mounting, a transverse tunnel formed to the tibial tunnel section with a cannulated set screw turned therein to engage the side of the tibial bone end.

FIG. 11 shows the patient's knee of FIG. 10 and utilizes the with the cannulated set screw 48 as fastener devices, the set screw blunt end 56 shown as having been turned snugly against the side of the femoral bone end 66, at approximately its mid-point, and the turning tool 49 removed. Shown therein the cannulated set screw coupling end 54 extends to slightly above the distal femur cortex surface. This is to facilitate a surgeon locating the cannulated set screw end and fitting the turning tool therein should it become necessary to remove the device. In practice, a cannulated set screw that is approximately seven (7) millimeters longer than the transverse hole formed from the bone cortex surface to the side of the femoral tunnel section 16 is preferred. Such set screw, when turned into the femoral tunnel section so as to bind the femoral bone end 66 therein, will leave a sufficient coupling end 54 portion to be accessible to the surgeon. To select which length of cannulated set screw 48 the surgeon, in forming the transverse hole 21 as shown in FIGS. 1 and 1A, observes the indices 22b marked along the twist drill 22 when it engages the bone cortex surface, and subtracts that indices from the indices 22b observed when the drill 22 enters the femoral tunnel section 16. The difference provides a measure of the length of the transverse hole 21 from the distal cortex surface to the femoral tunnel section. To which length approximately seven (7) millimeters is added to select an optimum length of cannulated set screw 48.

FIG. 11 also shows, in broken lines, the cannulated set screw 48 as having been turned into the transverse hole 24 formed from the side of the tibia 19b to intersect the tibial tunnel section 17. It should be understood that, the description of the forming of the tibial transverse hole 24, including its enlargement, and the fitting of the cannulated set screw 48 therein, is the same as described for forming the femoral transverse hole 21, its enlargement to transverse hole 21a, and the fitting and turning of the cannulated set screw 48 therein, as set out above. Except, the cannulated set screw 48 is first turned into the femoral transverse hole 21a to mount the femoral bone end 66 in the femoral tunnel section 16. Followed by applying a tensile force to the tibial bone end 67 prior to turning the cannulated set screw 48 into the tibial transverse hole 24 so as to engage and bind the tibial bone end in the tibial tunnel section 17. Which tensile force can be applied to the ligament graft as by turning a threaded device, not shown, into the tibial bone end and applying a pulling force thereagainst. This tensile force is maintained while the cannulated set screw is turned, as shown in broken lines, through the tibial transverse hole 24 and into engagement with the tibial bone end 67 of the ligament graft. Whereupon, the threaded device is turned out of and removed from the bone end.

Alternatively, as shown also in FIG. 11, a set screw 80, that may but need not be cannulated, can be turned, by fitting an appropriate tool in a screw rear end coupling 81, into the tibial tunnel section 17, alongside of the tibial bone end 67. So arranged, the set screw 80 is used as an interference screw for mounting the ligament graft tibial bone end in the end of the tibial tunnel section.

Figure 11A:
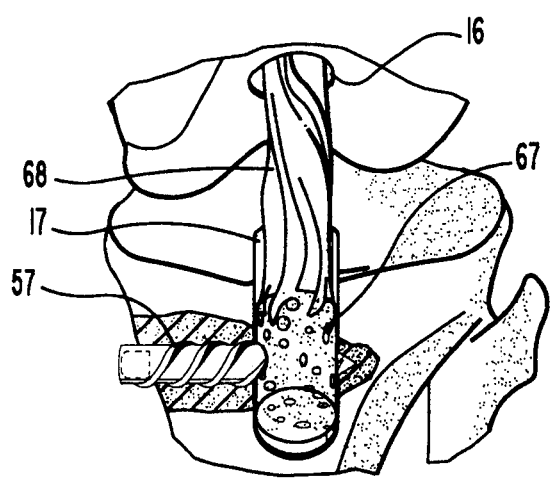
FIG. 11A is a view of the proximal tibia of FIG. 11 showing, in broken lines, a screw fitted through the tibial bone end illustrating a cross pin arrangement for mounting the ligament graft tibial bone end in the tibial tunnel section.

FIG. 11A shows still another arrangement for mounting the ligament graft tibial bone end in the tibia tunnel section. Therein the cannulated screw 57 is shown turned into the transverse hole 24, and passing through the tibial bone end 67 and into the opposite side of the tibial tunnel section 17. The cannulated screw 57 thereby provides a cross pin type mounting of the bone end in the tibial tunnel section.

Figure 12:
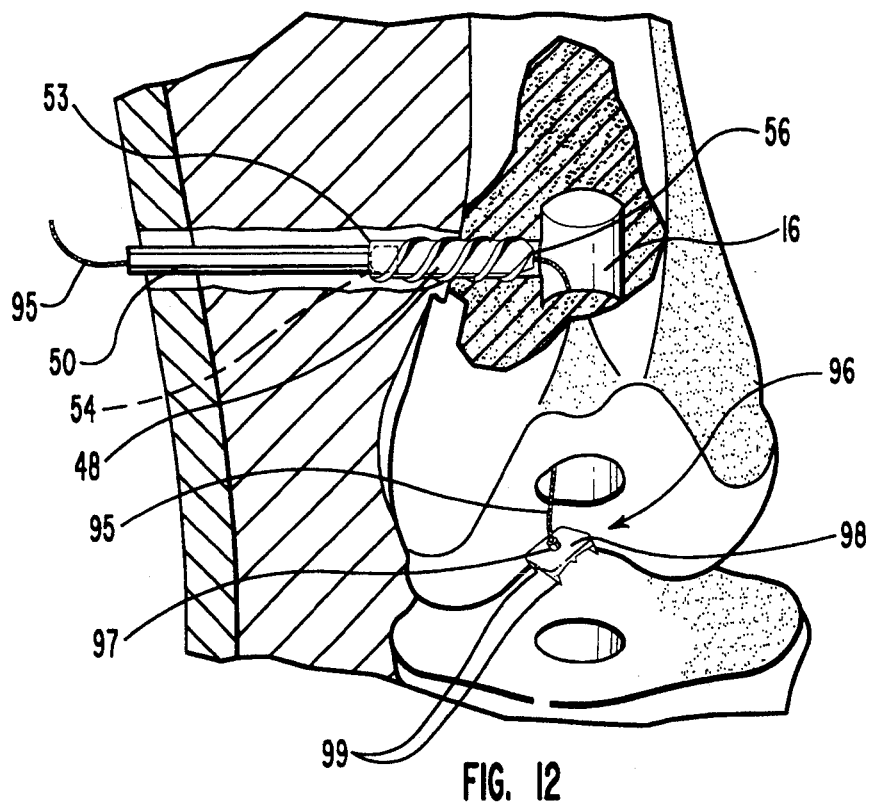
FIG. 12 shows a view like that of the distal femur of FIG. 11 showing the cannulated set screw turned into the transverse hole to where the screw end enters the femoral tunnel section, and showing a suture has having been threaded through the driver and set screw longitudinal passage that connects onto center post on a rear face of a cleated washer.
Figure 12A:
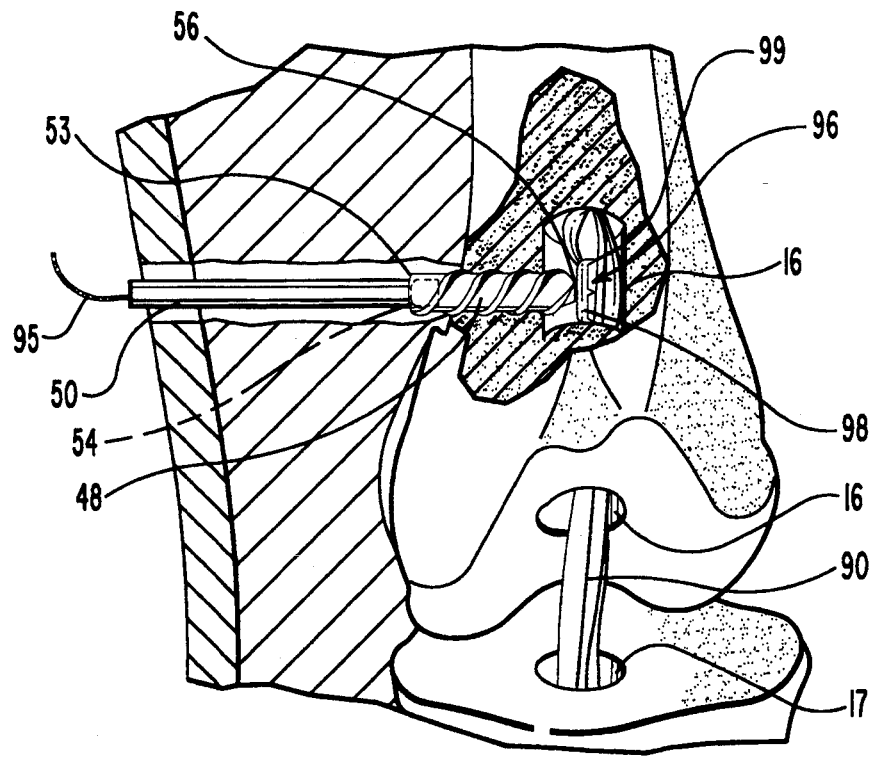
FIG. 12A is a view like FIG. 12 and additionally shows a semitendinosus ligament graft as having been fitted into the femoral tunnel section with the cleated washer shown as having been pulled onto the cannulated set screw end and showing the set screw as having been turned into the femoral tunnel section to where the washer cleats engage the graft side and urge it against the opposite femoral tunnel section wall.

In which mountings illustrated in FIGS. 11 and 11A the tibial bone end 67 of the ligament graft is placed under tension prior to its mounting within the tunnel section, utilizing one of the described fastener devices. Such application of a tensile force can involve a threaded device like that set out above, not shown, or other appropriate tool. Accordingly, the particular fastener device as is selected to mount the ligament ends needs to be compatible to the tool for applying a tensile force, and how it is used. Specifically, a utilization of the set screw 80 of FIG. 11 to provide such mounting could result in a diminishment of the tensile force applied to the tibial bone end 67 in that turning the set screw alongside the tibial bone end could urge it toward the knee intra articular joint, conflicting with the applied tension. In which situation the cannulated set screw 48 or cannulated screw 57 mounting, as shown, would be preferred.

Where the cannulated set screw 48 is set out above for use for mounting a bone tendon bone type ligament graft in a femoral or tibial tunnel section, it's use is not so limited. FIG. 12 shows another use of the cannulated set screw 48 for mounting a femoral end of the semitendinosus (soft tissue) ligament graft 90 of FIGS. 7B and 7C in the femoral tunnel section 16. FIG. 12 shows the cannulated set screw 48 end 54 mounted onto the end 53 of driver shaft 50 as having been turned into the transverse hole formed into the distal femur that intersects the side of the femoral tunnel section 16. So positioned, a suture 95 is threaded through the longitudinally passages of the driver shaft 50 and cannulated set screw 48 and into the femoral tunnel section, preferably from without the knee and into the femoral tunnel section. Whereat, the suture end is captured and is pulled through the femoral and tibial tunnel sections, 16 and 17, and out of the tibial tunnel section open end. The suture end is then fitted through and knotted at a hole in the end of a post 95 that extends at approximately a right angle from a mid-point of the back face 98 of a cleated washer 96. With the opposite or front face of the cleated washer including a plurality of spaced apart outstanding cleats 99. Shown in FIG. 12A the suture 95 has been pulled from the driver shaft 50, pulling the cleated washer therewith to where the cleated washer post 95 seats in the cannulated set screw longitudinal passage at blunt end 56. So arranged, turning the driver shaft 50 turns the cannulated set screw into the femoral tunnel section, the cleated washer 95 with cleats 99 extending therefrom leading the cannulated set screw. Turning of the set screw moves the cleats 99 into an end of ligament graft installed in the femoral tunnel section, the cleats entering the graft end as the washer urges it against the opposite tunnel section wall, endosteally mounting it. The ligament graft 90 can then be placed under tension by application of a pulling force to the opposite graft end, and the graft ends secured, as by stapling them onto the proximal tibia cortex, as shown in FIG. 7C, completing the mounting.

Hereinabove has been set out three fastener devices related hardware along with steps or procedures for the preparation of transverse holes that intersection the straight tunnel femoral and tibial tunnel sections for mounting the ends of a ligament graft in the straight ligament tunnel in a cruciate ligament replacement procedure. Of the described fastener devices, FIG. 11 shows the cannulated set screw 48 as having four flights of threads. A preferred cannulated set screw length is determined, as set out above, by a determination of the distance from the side of the femur or tibial to intersect the side of the respective femoral or tibial tunnel section, as set out above. The length of the cannulated screw 57 for use as the cross pin is, in turn, determined by the diameter of the tunnel section and the length required for it to extend across and lodge in the opposite tunnel section walls so as to provide a secure cross pin mounting. Which screw 57 as a cross pin, as required, may be selected to be long enough to extend slightly out from the bone cortex surface to be available to a surgeon fitting a tool therein to facilitate its removal, as required. Except for having a blunt end, the cannulated set screw 48 and cannulated screw 57 may be alike.

As set out above, a cannulated set screw and screw 48 and 57, respectively, along with the interference screw 80 and cross pin insert 80 are formed of a material suitable for human implantation, such as a tungeston steel, or the like, or, as appropriate, the fastèner device may be formed of a material such as polyglycolic acid to be reabsorbed by the body over time, eliminating any need for it being removed. To provide a fastener device that is suitable for functioning as the cannulated set screw 48, a screw that has wide threads that are spaced apart is preferred to provide a strong purchase when turned into the bone endosteum. For example, a cannulated set screw that has been found experimentally a practical embodiment of the cannulated set screw 48 has a length of approximately twenty one (21) millimeters, and a width of nine (9) millimeters, and is formed to have seven thread flights. Each such thread is spaced approximately three (3) millimeters apart, with each thread having a depth of approximately one and one half (1½) millimeters, and extend outwardly from a screw body that is approximately three (3) millimeters in width, the cannulated set screw having a width of approximately six (6) millimeters. Which screw threads provide a strong purchase when turned into the femoral and tibial endosteum. Also, as set out hereinabove, are referenced twist drills 22 and 27 that are for forming the femoral and tibial transverse holes 21 and 24. A preferred twist drill that is appropriate for a practice of the invention, is a two point five (2.5) millimeter twist drill that includes the indices 22b formed at spaced intervals along its length. Which twist drill 22 or 27 in the first embodiment of the invention is replaced with a K-wire that has approximately a one (1) millimeter diameter, that then guides a cannulated drill 47 that is approximately six (6) millimeters in diameter to enlarge the transverse holes to pass the cannulated set screw or cannulated screw 48 and 57, respectively therethrough. Which cannulated drill 47 and set screw 48 and screw 57, for use in the second embodiment of the invention with have a center longitudinal passage of sufficient diameter to slide along the twist drills 22 and 27. It should, however, be understood that, for some applications, the first drilling of transverse holes 21 and 24 could be made with the larger drill 47 or, as required, the transverse holes 21 or 24 could be left as originally drilled for receiving an appropriate fastener device turned therein.

Hereinabove has been set out preferred embodiments of a cross pin and set screw femoral and tibial fixation apparatus and method of the invention. It should, however, be apparent that this disclosure is made by way of example only, and that variations and modification to the described apparatus, the method for its use and functioning are possible within the scope of this disclosure without departing from the subject matter coming within the scope of the following claims and a reasonable equivalency thereof, which claims I regard as my invention.

I claim:

1. A method for mounting the ends of a bone tendon bone type ligament graft in femoral and tibial tunnel sections of a straight ligament tunnel in an arthroscopic surgical procedure for replacing a cruciate ligament comprising the steps of, utilizing a drill guide that is fitted into a straight ligament tunnel to guide drilling to a target location therein, using said drill guide to drill, with a first twist drill, a transverse hole from the medial or lateral side of the patient's knee to intersect the side of a femoral tunnel section of the straight ligament tunnel; removing the drill guide from the straight ligament tunnel and off of the first drill, leaving the first twist drill positioned in the transverse hole; fitting an axially open barrel of a soft tissue guide along the first twist drill to where a forward end of said barrel passes through the skin covering the patient's knee and engages the bone surrounding the transverse hole; removing the first twist drill and replacing it with a straight K-wire or rod; using said K-wire or rod as a guide, turning a cannulated fastener device along the length of the transverse hole through a side of the femoral tunnel section; fitting a femoral end of a ligament graft along the straight ligament tunnel to the end of the femoral tunnel section; turning said cannulated fastener to displace it into said femoral tunnel section to engage and mount said femoral end of said ligament graft therein inserting a cross pin means through said cannulated fastener and through said femoral end of said ligament graft; applying a tensile force to the tibial end of said ligament graft against the femoral end mounting so as to place said ligament graft in tension, and with a fastener device, fixing said tibial end in the tibial tunnel section of the straight ligament tunnel.

2. A method as recited in claim 1, wherein the drill guide has parallel external and reference rods with a web member connected between ends thereof forming a U-shape, and the reference rod is fitted into the straight ligament tunnel and includes a target thereon that is opposite to a guide sleeve mounting of the external rod such that the first twist drill fitted through a guide sleeve in said guide sleeve mounting and turned into the knee will contact the target on the reference rod, said drill guide arranged to allow for removal of the guide sleeve off from the first twist drill and the reference rod removed from the straight ligament tunnel.

3. A method as recited in claim 2, wherein the drill guide provides for release of the guide sleeve to allow it to be slid off of the first twist drill, and the external rod is slotted at the guide sleeve mounting to allow the first twist drill to slide therethrough, releasing the drill guide from the first twist drill and allowing the reference rod to be pulled from the straight ligament tunnel.

4. A method as recited in claim 3, wherein the drill guide includes a pair of guide sleeve mountings, each for receiving a guide sleeve releasably fitted therein, each guide sleeve for passing a first twist drill therethrough that is turned into the knee to form transverse holes into, respectively, the distal femur and proximal tibia to intersect the femoral and tibial tunnel sections, the guide sleeve mountings to be movable relative to one another, for intersecting a location in each of the femoral and tibial tunnel sections.

5. A method as recited in claim 1, further including, from a determination of the depth of penetration of the first twist drill to the side of the femoral tunnel section, determining the length of the transverse hole from the femur cortex to the femoral tunnel section and from that determination selecting a length of the cannula fastener device.

6. A method as recited in claim 5, wherein the first twist drill has a diameter of two point five (2.5) millimeters.

7. A method as recited in claim 1, further including passing a second twist drill along the K-wire to enlarge the transverse hole that is then pulled off from the K-wire prior to fitting and turning the cannulated fastener device along said K-wire.

8. A method as recited in claim 7, wherein the second twist drill as a diameter of six (6.0) millimeters.

9. A method as recited in claim 1, wherein the ligament graft includes a femoral bone end that receives a screw end of a straight wire turned into a femoral bone end undersurface whereto the tendon portion of said ligament graft is mounted, said straight wire for use by a surgeon to fit said femoral bone end into the tibial tunnel end, and to slide it therealong to contact the end of the femoral tunnel section in the femur endosteum.

10. A method as recited in claim 1, wherein the cannulated fastener device is a cannulated screw that is turned by a turning tool along the K-wire into the side of a femoral bone end of the ligament graft, urging said femoral bone end against the femoral tunnel section wall.

11. A method as recited in claim 1, wherein the cannulated fastener device is a cannulated screw that is turned by a turning tool along the K-wire and through a femoral bone end as an interference mounting of the ligament graft end.

12. A method as recited in claim 1, wherein the cannulated fastener device is a cannulated screw means that is urged along the K-wire to pass through a femoral bone end and said cross pin means extends across the femoral tunnel section as a cross pin for mounting the ligament graft end in the femoral tunnel section.

13. A method as recited in claim 12, wherein the cannulated screw means is a cannulated screw.

14. A method as recited in claim 1, wherein a screw is turned between a ligament graft tibial end and the tibial tunnel section wall providing an interference mounting therebetween.

15. A method as recited in claim 1, further including forming a transverse hole from the side of the patient's knee to intersect the tibial tunnel section; installing a K-wire therein; and, fitting and turning a cannulated fastener device along said K-wire to engage a ligament graft tibial end, mounting it in the tibial tunnel section.

16. A method as recited in claim 15, wherein both the femoral and tibial transverse holes are formed in a single positioning of the drill guide and the turning of first twist drills through a pair of guide sleeves that are mounted in the drill guide external rod, which drill guide is removable from said first twist drills and the straight ligament tunnel allowing said first twist drills to be replaced with K-wires that are then used for guiding femoral and tibial fastener devices therealong to engage the respective femoral and tibial bone ends of the ligament graft, mounting the bone ends in the femoral and tibial tunnel sections.

17. A method for mounting the ends of a bone tendon bone type ligament graft in femoral and tibial tunnel sections of a straight ligament tunnel in an arthroscopic surgical procedure for replacing a cruciate ligament comprising the steps of, utilizing a drill guide that is fitted into a straight ligament tunnel to guide drilling to a target location therein, using said drill guide to drill, with a first twist drill, a transverse hole from the medial or lateral side of the patient's knee to intersect the side of the femoral tunnel section of the straight ligament tunnel; removing the drill guide from the straight ligament tunnel and off of the first twist drill, leaving the first twist drill positioned in the transverse hole; using said first twist drill as a guide, turning a cannulated fastener device along the length of the transverse hole through a side of the femoral tunnel section; fitting a femoral end of a ligament graft along the straight ligament tunnel to the end of the femoral tunnel section; turning said cannulated fastener device to displace it into said femoral tunnel section to endosteally mount said femoral end of said ligament graft therein inserting a cross pin means through said cannulated fastener and through said femoral end of said ligament graft; applying a tensile force to the tibial end of said ligament graft against the femoral end mounting so as to place said ligament graft in tension, and with a fastener device, fixing said tibial end in the tibial tunnel section of the straight ligament tunnel.

18. A method as recited in claim 17, wherein the drill guide has parallel external and reference rods with a web member connected between ends thereof forming a U-shape, and the reference rod is fitted into the straight ligament tunnel and includes a target thereon that is opposite to a guide sleeve mounting of the external rod such that the first twist drill fitted through a guide sleeve in said guide sleeve mounting and turned into the knee will contact the target on the reference rod, said drill guide arranged to allow for removal of the guide sleeve off from the first twist drill and the reference rod removed from the straight ligament tunnel.

19. A method as recited in claim 18, wherein the drill guide provides for release of the guide sleeve to allow it to be slid off of the first twist drill, and the external rod is slotted at the guide sleeve mounting to allow the first twist drill to slide therethrough, releasing the drill guide from the first twist drill and allowing the reference rod to be pulled from the straight ligament tunnel.

20. A method as recited in claim 19, wherein the drill guide includes a pair of guide sleeve mountings, each for receiving a guide sleeve releasably fitted therein, each guide sleeve for passing a first twist drill therethrough that is turned into the knee to form transverse holes into, respectively, the distal. femur and proximal tibia to intersect the femoral and tibial tunnel sections, the guide sleeve mountings to be movable relative to one another, for intersecting a location in each of the femoral and tibial tunnel sections.

21. A method as recited in claim 17, further including, from a determination of the depth of penetration of the first twist drill to the side of the femoral tunnel section, determining the length of the transverse hole from the femur cortex to the femoral tunnel section and from that determination selecting a length of the cannula fastener device.

22. A method as recited in claim 21, wherein the first twist drill has a diameter of two point five (2.5) millimeters.

23. A method as recited in claim 17, further including passing a second twist drill along the first twist drill to enlarge the transverse hole that is then pulled off from the first twist drill prior to fitting and turning the cannulated fastener device along said first twist drill.

24. A method as recited in claim 23, wherein the second twist drill has a diameter of six (6.0) millimeters.

25. A method as recited in claim 17, wherein the ligament graft includes a femoral bone end that receives a screw end of a straight wire turned into a femoral bone end undersurface whereto the tendon portion of said ligament graft is mounted, the straight wire for use by a surgeon to fit it into the tibial tunnel end, and to slide said femoral bone end therealong to contact the end of the femoral tunnel section in the femur endosteum.

26. A method as recited in claim 17, wherein the cannulated fastener device is a cannulated screw that is turned by a turning tool along the first twist drill into the side of a femoral bone end of the ligament graft, urging said femoral bone end against the femoral tunnel section wall.

27. A method as recited in claim 17, wherein the cannulated fastener device is a cannulated screw that is turned by a turning tool along the first twist drill and through the femoral bone end as an interference mounting of the ligament graft end.

28. A method as recited in claim 17, wherein the cannulated fastener device is a cannulated screw means that is urged along the first twist drill, to pass through a femoral bone end and said cross pin means extends across the femoral tunnel section as a cross pin for mounting the ligament graft end in the femoral tunnel section.

29. A method as recited in claim 28, wherein the cannulated screw means is a cannulated screw.

30. A method as recited in claim 17, wherein a screw is turned between a ligament graft tibial end and the tibial tunnel section wall providing an interference mounting therebetween.

31. A method as recited in claim 17, further including forming a transverse hole from the side of the patient's knee to intersect the tibial tunnel section utilizing a first twist drill, and fitting and turning a cannulated fastener device along said first twist drill to engage a ligament graft tibial end, mounting it in the tibial tunnel section.

32. A method as recited in claim 31, wherein both the femoral and tibial transverse holes are formed in a single positioning of the drill guide and the turning of first twist drills through a pair of guide sleeves that are mounted in the external rod thereof, which drill guide is removable from said first twist drills and the straight ligament tunnel allowing said twist drills to be used for guiding femoral and tibial fastener devices therealong to engage the respective femoral and tibial bone ends of the ligament graft, mounting the bone ends in the femoral and tibial tunnel sections.

* * * * *